United States Patent
Tanghoej et al.

(10) Patent No.: US 9,682,212 B2
(45) Date of Patent: *Jun. 20, 2017

(54) MALE TELESCOPE CATHETER

(71) Applicant: Coloplast A/S, Humlebaek (DK)

(72) Inventors: Allan Tanghoej, Kokkedal (DK); Jens Berg Christensen, Hellerup (DK)

(73) Assignee: Coloplast A/S, Humlebaek (DK)

(*) Notice: Subject to any disclaimer, the term of this patent is extended or adjusted under 35 U.S.C. 154(b) by 1210 days.

This patent is subject to a terminal disclaimer.

(21) Appl. No.: 13/721,046

(22) Filed: Dec. 20, 2012

(65) Prior Publication Data
US 2013/0218136 A1 Aug. 22, 2013

Related U.S. Application Data

(63) Continuation of application No. 11/666,225, filed as application No. PCT/EP2005/055555 on Oct. 25, 2005, now Pat. No. 8,361,057.

(Continued)

(30) Foreign Application Priority Data

Oct. 25, 2004 (DK) .............................. 2004 01634
Jul. 15, 2005 (DK) .............................. 2005 01047

(51) Int. Cl.
*A61M 25/00* (2006.01)
*A61M 25/01* (2006.01)

(52) U.S. Cl.
CPC ........ *A61M 25/0017* (2013.01); *A61M 25/00* (2013.01); *A61M 25/0054* (2013.01);

(Continued)

(58) Field of Classification Search
CPC .............. A61M 25/00; A61M 25/0017; A61M 2025/0175; A61M 2025/0004;

(Continued)

(56) References Cited

U.S. PATENT DOCUMENTS 2,613,988 A * 10/1952 Jarbeau ................ B65D 77/283
215/388
3,344,791 A * 10/1967 Foderick ............... A61M 25/04
604/104

(Continued)

OTHER PUBLICATIONS

Examiner's Answer for case 13389753, mailed Aug. 27, 2015.*

*Primary Examiner* — Adam Marcetich
(74) *Attorney, Agent, or Firm* — Coloplast Corp., Coloplast A/S; Nick Baumann

(57) ABSTRACT

A catheter includes a proximal section that is inserted into and telescopically movable relative to a distal section. A proximal end of the proximal section is insertable into a urethra of a user and the distal section provides a discharge conduit for urine. The proximal section includes a rear portion, and an exterior surface of the rear portion diverges away from the proximal end to provide a diverging rear transition section that is wider than the proximal end of the proximal section. The distal section includes a front portion and an interior surface of the front portion converges to an opening formed in a front transition end, the opening is narrower than the diverging rear transition section of the proximal section.

11 Claims, 15 Drawing Sheets

Related U.S. Application Data

(60) Provisional application No. 60/699,366, filed on Jul. 15, 2005.

(52) U.S. Cl.
CPC .............. *A61M 2025/0004* (2013.01); *A61M 2025/0175* (2013.01)

(58) Field of Classification Search
CPC ...... A61M 25/0054; A61M 2025/0006; A61M 2210/1089; A61M 2210/1096; F16B 7/1463; F16B 7/10; F16B 7/105; A47G 21/189; B29L 2023/008
See application file for complete search history.

(56) References Cited

U.S. PATENT DOCUMENTS

| | | | | |
|---|---|---|---|---|
| 3,615,595 A * | 10/1971 | Guttag | .................. | A23L 27/74 426/85 |
| 3,740,034 A * | 6/1973 | Scroggins | ............ | A63D 15/086 16/429 |
| 4,419,025 A * | 12/1983 | Takahashi | ............... | F16B 7/105 16/429 |
| 4,657,182 A * | 4/1987 | Hoshi | .................. | A47G 21/189 239/33 |
| 4,688,721 A * | 8/1987 | Inaba | .................. | A47G 21/189 239/33 |
| 4,736,887 A * | 4/1988 | Inaba | .................. | A47G 21/189 239/33 |
| 4,850,533 A * | 7/1989 | Hoshi | .................. | A47G 21/189 239/33 |
| 5,104,384 A * | 4/1992 | Parry | .................. | A61M 5/3271 604/192 |
| 5,772,636 A * | 6/1998 | Brimhall | ........... | A61M 25/0631 604/164.01 |
| 5,792,122 A * | 8/1998 | Brimhall | ........... | A61M 25/0631 604/164.01 |
| 5,921,586 A * | 7/1999 | Prassas | .................... | F16L 47/00 285/12 |
| 2003/0105451 A1* | 6/2003 | Westlund | .......... | A61M 25/0021 604/532 |
| 2004/0116850 A1* | 6/2004 | Schneider | ......... | A61M 25/0606 604/96.01 |
| 2006/0020165 A1* | 1/2006 | Adams | ............... | A61B 1/00094 600/121 |

\* cited by examiner

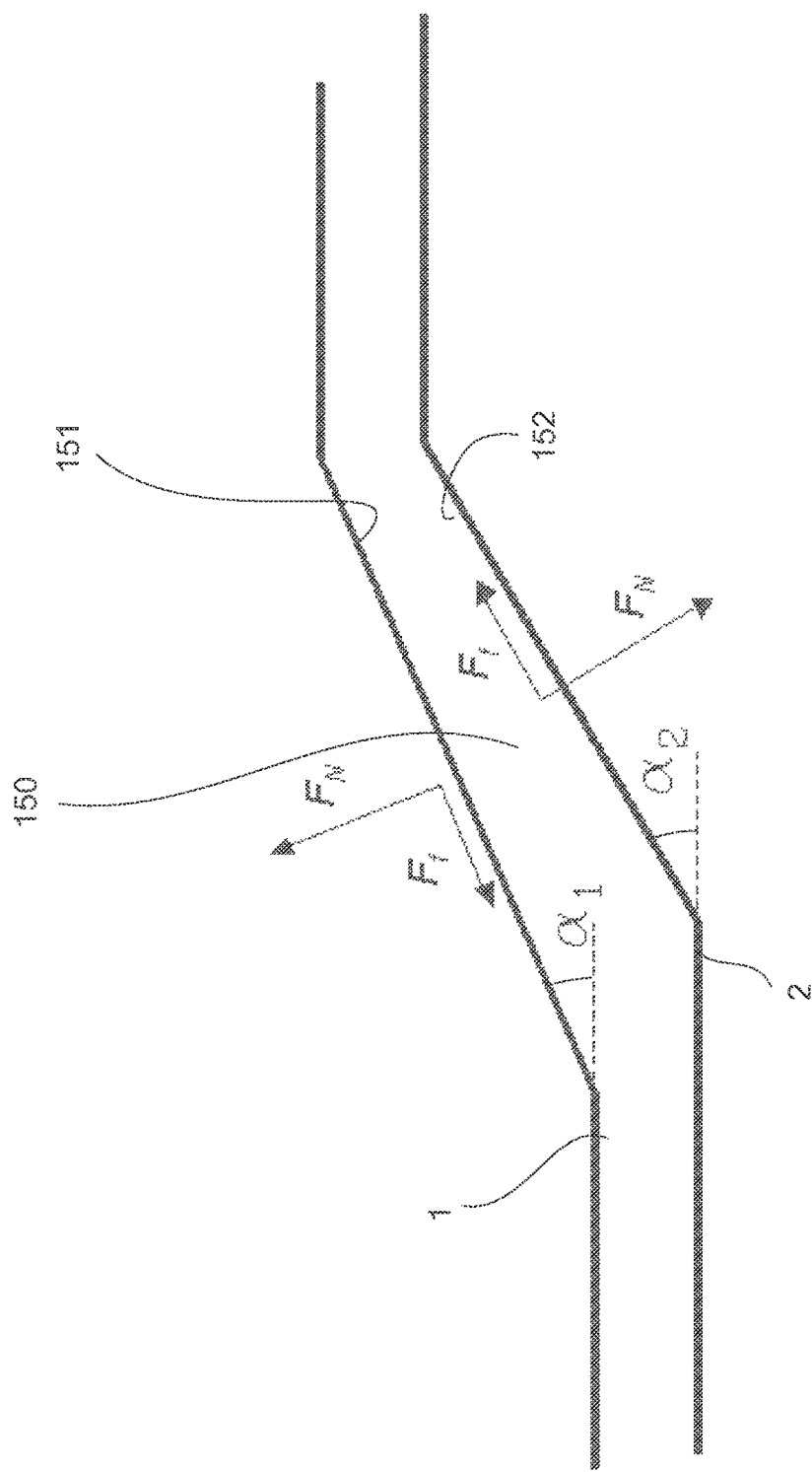

MALE TELESCOPE CATHETER

FIELD OF THE INVENTION

The present invention relates to a catheter, especially an expandable catheter with a transition between the individual sections allowing insertion of the transition into urethra.

BACKGROUND

A certain flexibility of a catheter is needed to pass through the curvature of the urethra. Normally a catheter is made of the same, flexible, material all the way through. When reaching some resistance when pushed through the urethra, the part of the flexible tube not yet inserted tend to bend. The user will often touch the catheter tube by hand to aid insertion; thereby increasing the risk of urinary tract infections.

It is also a commercial reality that male catheters take up more space than convenient to the user, either at home or on the road.

To comply with the desire for less space consuming catheters, especially catheters having a collapsible, or otherwise space reducing, insertable part is needed. Different types of telescopic catheters have furthermore been disclosed in the art.

U.S. Pat. No. 6,592,567 disclose a kidney perfusion catheter assembly having an introducer catheter and a catheter tip. The catheter tip moves coaxially in the distal end of the introducer catheter. The tip may be retracted within the introducer catheter or telescopically extended from the distal end of the introducer catheter component.

U.S. Pat. No. 4,632,668 discloses an extendable/retractable ventricular catheter which is essentially a two-piece telescoping assembly with a distal catheter slideably extending from within a proximal catheter. When the distal catheter is extended to its maximum length from within the proximal catheter, the two pieces are prevented from coming apart by the distal catheter having an external locking means and the proximal catheter having internal locking means.

However, urinary catheters must be extended before insertion and thereby needs to be locked in such a way that the catheter to do not collapse during insertion. WO 03/002179-A2 discloses a kit for preparing a catheter for draining a human bladder, the kit comprising at least two catheter sections defining a passage therein, the sections being adapted to be arranged in such a mutual configuration that the passages are joined into one passage and the sections together constitute a catheter of a length larger than the length of each individual section and having such rigidity that the entire catheter can be manipulated by manipulation of one of the sections individually. In particular, WO 03/002179-A2 is concerned with a catheter in which a first section is insertable into the urethra and a second separate section is suitable for external manipulation.

DETAILED DISCLOSURE

It is an object of the invention to provide a collapsible catheter with a relatively long insertable length. Accordingly, the invention, in a first aspect, provides a catheter which is operable between a collapsed configuration for storage and transportation and an expanded configuration for draining fluid from a body via a conduit which extends axially in a longitudinal direction from a proximal end to an opposite distal end, the catheter comprising: a proximal section, adapted to be fully inserted into a urinary channel of the body and forming a proximal part of the conduit which part extends axially between the proximal end and a first transition end of the proximal section, and a distal section, adapted to be at least partially inserted into the urinary channel and forming a distal part of the conduit which part extends axially between a second transition end of the distal section and the distal end, an insertable part of the first transition end being dimensioned to enable its positioning inside a receiving portion of the distal part of the conduit to enable axial movement of the sections relative to each other to operate the catheter between the collapsed configuration and the expanded configuration of the catheter, wherein the sections comprise cooperating coupling structures to support the catheter in the expanded configuration.

This allows for an expandable catheter where the insertable catheter part, i.e. both the proximal section and the distal section, is telescopically retractable and expandable between a collapsed configuration and an expanded configuration. The catheter advantageously consumes less space in the collapsed configuration than in the expanded configuration. Thus, a catheter is provided which takes up less space when stored or transported in its collapsed configuration. This allows for reduced space consumption during transport and also for improved life quality for the user of catheter as such expandable catheters can be stored more discreetly.

The term collapsed configuration of the catheter according to the invention should be understood broadly as any configuration where the axial extent of the catheter is smaller than the expanded configuration wherein the coupling structures of the distal section and proximal section couples the catheter into an expanded configuration. By coupling is understood that it requires a larger force to move the catheter from the expanded configuration to the collapsed configuration than to move the catheter oppositely from the collapsed configuration to the expanded configuration.

Furthermore, a catheter where the insertable part is collapsible is especially advantageous for male users, as their urethra is considerably longer compared to urethra of female users. However, the present invention may also be used for the insertable part of a female catheter.

During use, the catheter is brought to the expanded configuration and the proximal end is guided into the urethra. Subsequently, the sections are inserted until urine starts to flow through the conduit.

In one embodiment the sections are provided so that a first longitudinal directed force required for moving the catheter from the expanded configuration to the collapsed configuration is larger than a second longitudinal directed force required for at least one of the proximal section and the distal section to bend.

The coupling may e.g. be rigid enough to enable insertion and optionally curling up of the catheter in a container, without moving the catheter to the collapsed configuration. This may also increase the safety against collapsing of the catheter during insertion of the sections into the urethra. The push-in force required to insert the catheter into the urethra is approximately 1 N. In one example, the catheter coupling resists a force in the range of 5-10 N, and the same catheter bends out or kink at a longitudinal force in the range of 2-3N. I.e. the catheter bends or kink prior to the release of the coupling, and to move the catheter to the collapsed state, the sections must be manipulated from a position very close to the transition ends of the sections. As an example, the catheter could be made so that it can only be moved to the expanded configuration and so that attempts to move it back destroys the catheter and thus makes it unusable for further use.

In an alternatively embodiment the sections are provided so that a first longitudinal directed force required for moving the catheter from the expanded configuration to the collapsed configuration is smaller than a second longitudinal directed force required for at least one of the proximal section and the distal section to bend.

This provides for an expandable catheter, which can be easily collapsed after use in a controlled fashion as it will collapse into its collapsed configuration wherein it can be contained until disposal. In this embodiment, it is desirable that the force which is required to collapse the catheter is higher than the force required to insert the catheter into the urethra. I.e. the coupling is sufficiently strong to maintain the expanded configuration during the bending of the catheter as enters through the curved passage of the urethra, in particular of mail users. After use, when the catheter is removed from the urethra, the coupling should, on the contrary, allow collapsing of the catheter by pushing the two sections towards each other, and the movement towards the collapsed configuration should preferably take place prior to kinking of the catheter.

In one embodiment the proximal section forms a first outer surface with a circumference which increases from the proximal end towards the first transition end and/or the distal section forms a second inner surface with a circumference which decreases from the distal end towards the second transition end. In particular, the distal section may decrease to a circumference which is smaller than the circumference of the transition end of the proximal section. This provides a simple stop whereby the distal section and the proximal section may not be pulled apart when the catheter is in the expanded configuration.

In order to provide a smooth fit or alternatively simple coupling structures the first outer surface may form a first angle to the longitudinal direction, and the second inner surface may form a second angle to the longitudinal direction, the first angle being at least of the size of the second angle. When the angles are the same size, the inner surface of the distal section and the outer surface of the proximal section may join in parallel planes, and when the first angle is larger than the second angle, the surfaces may join by a slight deformation when the two sections are pulled tightly towards the expanded configuration. Accordingly, the transition ends of the sections or at least the transition end of one of the sections may preferably be deformable by pulling the sections towards the expanded configuration by hand.

To facilitate the coupling of the sections, one of the proximal and distal sections may comprise a protrusion cooperating in the expanded configuration with a depression of the other one of the proximal and distal sections. This provides easy produced coupling structures which allow the distal and proximal section to engage and thereby to lock the catheter in the expanded configuration.

The depression may form a circumferentially extending slot in an outer surface of the section in question. The slot may for example be provided in an outer surface of the proximal section. The slot may have any cross-sectional shape. However, a relatively sharp edged shape, e.g. a V-shape or a U-shape when seen in a longitudinal cross-section may serve to retain the protrusion. In particular, the protrusion may have a. shape which is similar to the shape of the slot.

The outer surface and the inner surface of both the proximal section and the distal section may have different shapes, be formed with a number of local shapes, such as corresponding protrusions and indents, or more general shapes covering larger areas, such as sloping faces etc. Such shapes and forms may be provided in order to provide different functions, for example coupling structures or improved sliding surfaces.

Although such coupling structures typically will be formed as circumferentially extending shapes and formations having a continuous circumference in order to provide sealing means, they may also be provided as local bulges or the like having limited extent in all directions.

In one embodiment of the catheter according to the invention the distal section comprises an inner surface portion which forms a part of a wall of the conduit in the second transition end, which inner surface portion forms a distance, a, to a centre axis, and the proximal section comprises an outer surface portion being adjacent to the insertable part, which outer surface portion forms a distance, b, to the centre axis, wherein b is larger than a.

In the present invention catheters are typically formed of tubes having a circular cross section. A change in the dimensions of different surface portions of the tube, i.e. the distance from the tubes centre axis to the corresponding surface portions, will correspond to the tubes radius or diameter in that respective portion. However, when the tube is deformed or catheters having different cross sectional shapes are used the term radius, diameter or distance from the surface portion to the centre axis may not always be unambiguously used. Alternatively it can be said, that the respective surface portions may have different circumferences to indicate a change in the surface corresponding to a change of the radius or diameter of a tube having a circular cross section.

In order to thereby provide a protruding rim, an upwardly sloping surface the proximal section may thus comprises an outer surface with a first surface portion with a first circumference which first surface portion, in the longitudinal direction, is followed by a second surface portion with a second circumference which is larger than the first circumference.

Additionally in order to for example forming above mentioned slot the second surface portion, in the longitudinal direction is followed by a third surface portion forming the slot and having a third circumference being smaller than the second circumference.

To completely define the slot, the slot can be followed by a fourth surface portion with a fourth circumference being larger than the circumference(s) of the third surface portion.

In order to support the position of the proximal section relative to the distal section the protrusion may form a circumferentially extending key adapted to cooperate with the slot in the expanded configuration.

In one embodiment the key forms a fifth surface portion which protrudes from an inner surface of the distal section. Additionally the fifth surface portion may have a circumference which is smaller than the circumference of the remaining inner surface of the distal section.

In one embodiment, in order for the key and slot to couple, the fifth surface portion has a circumference which is smaller than the circumferences of the second and fourth surface portions.

In another embodiment of the catheter according to the invention a gap is formed between the third surface portion and the fifth surface portion in the expanded configuration and/or between the first surface portion and the fifth surface portion in the collapsed configuration. Advantageously such a gap prevents that the fifth portion, typically defined by the key, scrapes against the first and third second surface portions. In particular this is advantageous when the catheter is hydrophilic coated whereby it is avoided that the third surface scrapes of the coating when the gap contains a hydrophilic fluid, a hydrogel or other type of fluid coating.

It has furthermore surprisingly shown that the hydrophilic coating, or alternatively gel coating, function as suspension mean between the fifth surface portion and the first and third surface portion respectively. In other words, the coating suspends the fifth surface around the first or fifth surface portion respectively evenly providing an evenly disposed gap around the corresponding circumference.

Furthermore, especially when using gel coated catheters, the key may advantageously function as distributor, to evenly distribute the gel around the proximal section when the catheter is moved from its collapsed position to its expanded position.

In order to further reduce the risk of scraping off the hydrophilic coating and to protect the mucosa, at least the transition ends of the sections are circular in a cross-section perpendicular to the longitudinal direction, thereby create a smooth transition.

It should be understood that the proximal section and the distal sections do not necessarily needs to be formed of one single element. Due to for example production limits, production costs, material characteristics etc, the individual elements can be made of a number of separate parts.

Thus, in one embodiment of the catheter according to the invention the proximal section comprises: a tubular member forming the proximal end of the catheter, and a sleeve with an outer surface with a sixth surface portion and a seventh surface portion, the circumference of the sixth surface portion being larger than the circumference of the seventh surface portion, the sleeve being inserted into a conduit so that the seventh surface portion is in contact with an inner surface of the tubular member and the sixth surface portion forms an outer surface of the proximal section.

Alternatively the sixth surface portion has a larger circumference than the outer surface of the tubular member, which provides a raised area, for example a rim, on the proximal section.

The seventh surface portion may furthermore comprise an enlarged surface portion in which the circumference is larger than in the remaining part of the seventh surface portion. This advantageously provides improved means for holding the sleeve and tubular member assembled.

Additionally a material of the tubular member and a size of the enlarged surface portion may be chosen so that the enlarged surface portion deforms the outer surface of the tubular member and forms a protrusion on that surface. This provides a curved bulb on the outer surface of the tubular member. Furthermore, by providing a rim between the sixth surface portion and the tubular member as mentioned above, a slot as described earlier may be provided.

Likewise may the distal section also comprise of different members. For example in one embodiment the distal section comprises: a tubular member forming the distal end of the catheter, and a sleeve with an outer surface with a eighth surface portion and a ninth surface portion, the circumference of the eighth surface portion being larger than the circumference of the ninth surface portion, the sleeve being inserted into a conduit so that the ninth surface portion is in contact with an inner surface of the tubular member and the eighth surface portion forms an outer surface of the proximal section. The sleeve may thus partly function as a support member, where the ninth surface portion provides improved support for the tubular member. Furthermore, a part of the sleeve will extend inwards from the ninth surface portion and thereby forms a key, which may engage with a respective slot on a proximal section as described earlier.

In order to provide a smooth transition between the proximal section and the distal section when the catheter is in the expanded configuration, the sleeve may form the second transition end of the distal section and wherein the eighth surface portion has a circumference which decreases towards the second transition end.

Within the scope of the invention many different embodiments and alternative solutions may be provided.

Thus, the present invention may also relate to an expandable catheter comprising a proximal section and a distal section, both sections forming a part of a conduit, the proximal section comprising an insertion end for insertion into an opening with an aperture for draining a fluid into the conduit, the conduit extending towards an opposite transition end, the proximal section having an outer circumference which increases (A) towards the transition end, and the distal section comprising a transition end receiving fluid from the transition end of the proximal section into the conduit when the catheter is expanded, the conduit extending toward an opposite guiding end, the distal section having an outer circumference which decreases towards a transition end, the transition end of the proximal section being dimensioned to enable its positioning inside the conduit of the distal section to enable movement of the sections relative to each other.

An inserted surface coated catheter is pulled out of location in the urethra with a force of about 0.2 N. For an uncoated catheter, this pull-out force is in the range of 2 N. It is much preferred that the transition between the two sections of the catheter is constructed such that the transition will endure the pull-out force. Otherwise, the catheter could separate into two pieces and the proximal section remain in the urethra.

Typically, the force required to insert a catheter, the push-in force, is about 1 N for a coated catheter. Thus, it is much preferred that the transition between the two sections of the catheter is constructed such that the transition will endure the push-in force.

Otherwise, the catheter could collapse into the non-expanded state during insertion. As a rule of thumb, the ability to endure the push-in force must be so that the catheter will tend to bend when exposed to high push-in forces, before it will tend to collapse into the non-expanded state. It is our experience that forces of more than 10 N are not required to insert a catheter.

In one embodiment the elasticity of the transition end of the proximal section is less than the elasticity of the remaining part of the proximal section. With a lower elasticity is understood that this part of the proximal section is less flexible, less bendable, and less compressible than the remaining part of the proximal section.

In one embodiment the elasticity of the transition end of the distal section is lower than the elasticity of the remaining part of the distal section. In a related embodiment, the transition end of the distal section, with a lower elasticity, is followed by (moving towards the proximal end) a segment constituting the tip of the distal transition part.

As E-modulus is a constant describing the material, a simple way of obtaining a segment with decreased elasticity is to increase the wall thickness. However, the same can be obtained by using another material with high e-modulus.

In one embodiment, the outer circumference of the transition end of the proximal section is larger than the inner circumference of the transition end of the distal section. By this arrangement is achieved endurance during the pull-out force. However, in order to make sure that the transition end of the proximal section can be positioned inside the conduit of the distal section and to enable movement of the sections relative to each other, the outer circumference of the transition end of the proximal section is preferably less than the inner circumference (the conduit circumference) of the distal section. This is one example of how the proximal section can be adapted to be displaceable arranged within the distal section.

In one embodiment, the transition end of the distal section and the transition end of the proximal section of the catheter are conically shaped. When drawn together during expansion of the telescopic catheter, the two conically shaped transition ends will grab and lock each other. The grab and lock is affected by:

- the angle between the longitudinal direction of the catheter and the conical direction (see FIG. 1, (7) and (8)). An acute angle (less than 90°) will secure locking between the two sections. The more pointed, the better the lock between the two sections. Thus, the angle is preferably less than 40°. Due to the tubular dimensional restrictions, such acute angle will optimize the length of material in contact with each other and thereby increase the frictional force obtained.
- the deformation of the materials. The higher the E-modulus of each of the two sections, the less the material will deform during the expansion, and it will be harder to separate the sections after the transition ends have grabbed and locked each other during expansion of the telescopic catheter.
- thickness of the materials. It is preferred that the thickness of the distal section is as thin as possible, so the transition is as small as possible. Preferably the distal section is 0.35 mm in wall thickness. The proximal sect ion is preferably between 0.4 and 1 mm in wall thickness.

In one embodiment a third element is attached to at least one of the conical surfaces. This third element can indirectly modulate the elasticity of the transition ends, allowing a secure grab and lock, without compromising the aforementioned requirements.

When in use, the catheter is expanded by pulling the two sections in opposite directions and secured. That is, the conical shape of the distal section is deformed (expanded) when the conical shape of the proximal section is inserted. Likewise, the conical shape of the proximal section is deformed (compressed) when the conical shape of the distal section is draw over it. The grab and lock features will secure endurance during both the pull-in force and the push-out force, and the proximal transition end is wedged inside the distal transition end when the catheter is fully expanded. This set of embodiments is especially preferred for catheters without coating, that is for catheters were a substantial friction force is generated between the distal- and proximal sections.

However, for coated catheters, typically with a friction coefficient ($\mu$) around 0.05, the friction force generated during use will not be sufficient to hold the sections together so they that do not collapse during insertion, and/or to prevent them from separating.

In the conical contact zone, at the interface between the transition ends of the proximal and distal sections—if for simplicity looking at a cross section—the resulting force acting between them—can be divided into a normal force $F_N$ (perpendicular to the contact surface) and a friction force $F_f$ (tangential to the contact surface). If considering Coulomb friction, the relation between the friction force and the normal force can be described by; $F_f = \mu \cdot F_N$, where $\mu$ is the friction coefficient.

In dry conditions the friction coefficient will be high (e.g. for polyurethane expectedly at least $\mu=0.5$ and probably even higher than 1). As a result the friction force will be comparable to the normal force—and as a consequence the force to separate the proximal and distal sections will be high—even for small conical angles $\alpha$ (where the friction force is close to parallel to the separation force acting along the longitudinal axis of the catheter). For simplicity this can be illustrated by considering one embodiment in cross section (where $\alpha_1$ (7)=$\alpha_2$ (8)). Here the separation force can be described by the horizontal components of the sum of the normal force and the friction force (referring to FIG. 15):

$$\text{Separation force}(F_{sep}) = \cos(\alpha) \cdot F_f + \sin(\alpha) \cdot F_N =$$
$$\cos(\alpha) \cdot \mu \cdot F_N + \sin(\alpha) \cdot F_N = (\cos(\alpha) \cdot \mu + \sin(\alpha)) \cdot F_N$$

As seen from this equation—if $\mu$ is close to 0—a high separation force can only be obtained either by:
a. having an angle $\alpha$ close to 90 deg, or
b. by ensuring that very high normal forces $F_n$ can be sustained by both the distal and proximal sections in contact.

In one embodiment of the invention, the angle $\alpha$ is over 70°, such as between 70° and 90°, between 80° and 90° or even between 85° and 90°. In these embodiments, the shape of the proximal section, is a T-shape.

In one embodiment of the invention, the angle $\alpha$ is over 90°, such as between 90° and 130°.

In one embodiment, the distal transition part and the proximal transition parts are secured by mechanical means. One such example is wherein an element passes a bulb allowing passage in one direction but not in the other. One such example is disclosed in Example 4. This is especially preferred along with catheters with and angle $\alpha$ of about 90°, as that angle will secure endurance during the pull-out, whereas a bulb will secure endurance during the push-in. In one embodiment the bulb is placed on the outside of the proximal section. This bulb will also have the function to aid in providing a smooth transition. In another embodiment, the bulb is placed on the inside of the distal section. In the embodiment where the catheter is coated, the bulb on the outside might be left without coating when the catheter is ready for use and the tip of the distal section has passed the bulb. Thus, in a preferred embodiment, the bulb is placed on the inside of the distal section. To obtain maximal endurance during push-in, a bulb is placed on both sections.

Another such example is applying one end of a plurality of hairs to either, or both, transition parts. On the proximal part the other end of those hairs are left pointing distally. On the distal part the other end of those hairs are left pointing proximally. Hereby, the sections will slide smoothly across each other (running along the direction of the hairs), but will experience substantially higher resistance sliding the other way (against the direction of the hairs).

The mucosal inside of the urethra comprises a number of folds in the longitudinal direction, along with normal urine flow. These mucosal folds are sensitive to sharp or pointed parts of a catheter that will damage the mucosa causing pain and bleeding. It is therefore preferred that the exterior of the transition between the two sections of the catheter according to the invention is smooth. Smooth, in this context is intended to mean that it is smooth enough not to damage the mucosa. Especially, the actual point of transition, that is where mucosal exposure to the proximal section stops and mucosal exposure to the distal section begins. Such smoothness is obtained in one of the ways described below, or a combination thereof:

the tip of the distal transition part is rounded, such that no sharp edges are present.

the point where the distal section goes from a tube to a conical shape is rounded, such that no sharp edges are present. Alternative shapes are concave, convex and straight.

eliminating the gap (0.15 to 0.2 mm in radius) between the proximal and distal sections, at the transition end. This can be done by increasing the diameter of the proximal section locally at the transition end to obtain a close fit with the hole in the distal end of the distal section (see FIG. 15).

a bulb is provided on the outer surface of the proximal tube, just proximally to the transition section. This bulb will 'lift' the mucosa to avoid contact with the point of transition. Furthermore, such bulb will act as a mechanical lock between the distal and the proximal section of the catheter allowing passage in one direction but not in the other.

the thickness of the distal transition section is decreased to a thin foil of between 0.02 mm to 0.1 mm. preferably between 0.05 to 0.1 mm. The less thickness of this distal transition section, the less the difference in the point of transition.

In one embodiment of the invention the catheter is coated to provide a slippery surface for easy insertion. In order to prevent that this coating is damaged during extension of the catheter, it is preferred that the open hole in the tip in the transition end of the distal section is slightly bigger, such as 0.15 mm bigger, or 0.2 mm bigger, than the outer diameter of the tube in the proximal section. Thereby touching of surface by the tip is limited.

In one embodiment the elasticity of the distal section is different from the elasticity of the proximal section, thereby controlling which section is deformed when a force is applied. The proximal section preferably has an elasticity comparable to that known from common catheters, to allow passage through urethra, prostate and sphincter. The distal section preferably has a lower elasticity than the proximal section, this is needed not to bend during insertion, withstanding the push-force.

It is preferred that the proximal section is of the thickness commonly used for catheters, that a wall thickness is between 0.4 mm and 1 mm. It is preferred that the distal section is about 0.35 mm.

It is preferred that each of the two sections are between 70 and 230 mm The expanded catheter will have a total length of between 250 mm and 360 mm.

It is preferred that the proximal section has a length between 150 mm and 230 mm. This allows the proximal section to be inserted through urethra, and the transition to the distal section being close to insertion (or just inserted) such that the distal section with the high e-modulus (and more stiff part) will withstand the slightly higher force needed to insert the catheter through prostate and sphincter. The distal section is preferably with a length between 100 mm and 130 mm.

BRIEF DESCRIPTION OF THE DRAWINGS

FIG. 15 shows schematically forces exerted on an embodiment of the catheter according to the invention.

DETAILED DESCRIPTION OF PREFERRED EMBODIMENTS

Figure 1:
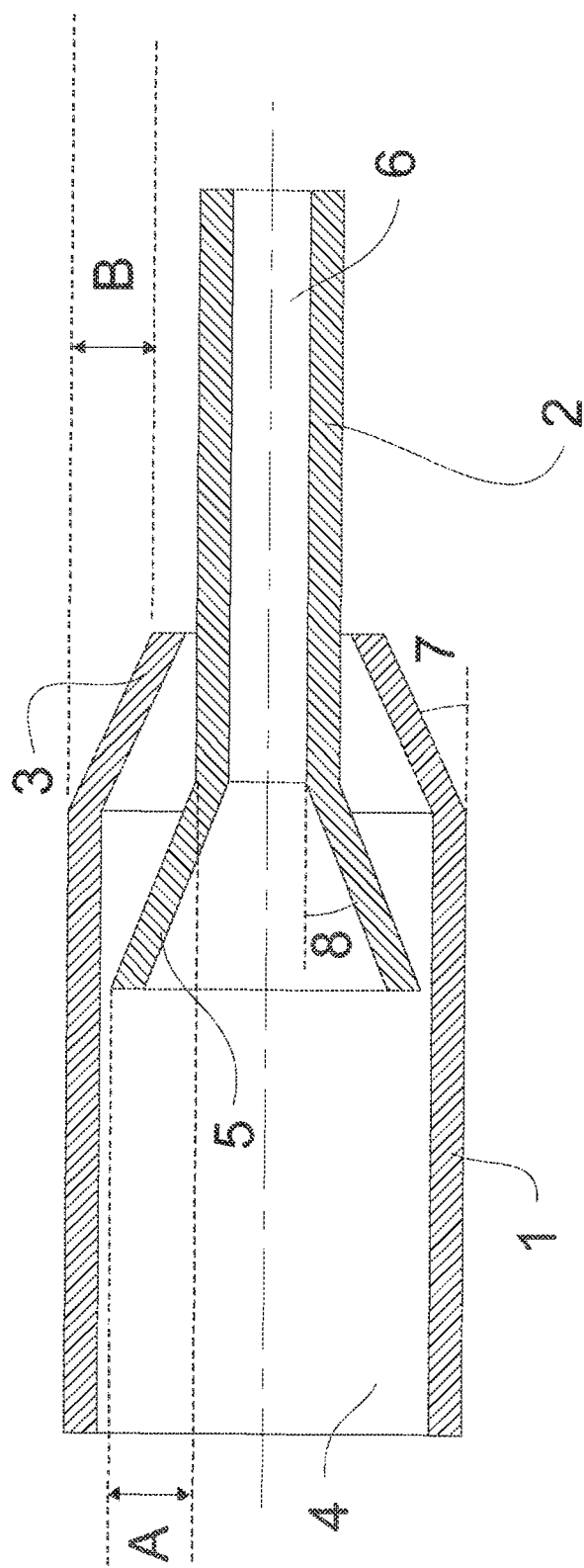
FIG. 1 shows a first embodiment of an expandable catheter according to the invention seen in cross section along a longitudinal axis.

In the following, preferred embodiments of the invention will be described in further details with reference to the drawing in which FIG. 1 shows a telescopic catheter, with a distal 1 and a proximal section 2. The distal section 1 has a transition end 3 and a proximal guiding end 4. The proximal section 2 has a transition end 5 and a distal insertion end 6. The angle between the longitudinal direction of the catheter and the conical erection on the distal section is marked 7. The angle between the longitudinal direction of the catheter and the conical erection on the proximal section is marked 8. The transition end of the proximal section has an outer diameter which is higher than the remainder of the proximal section (the difference A). The transition end of the distal section has on outer diameter which is smaller than the remainder of the proximal section (the difference B).

Figure 3:
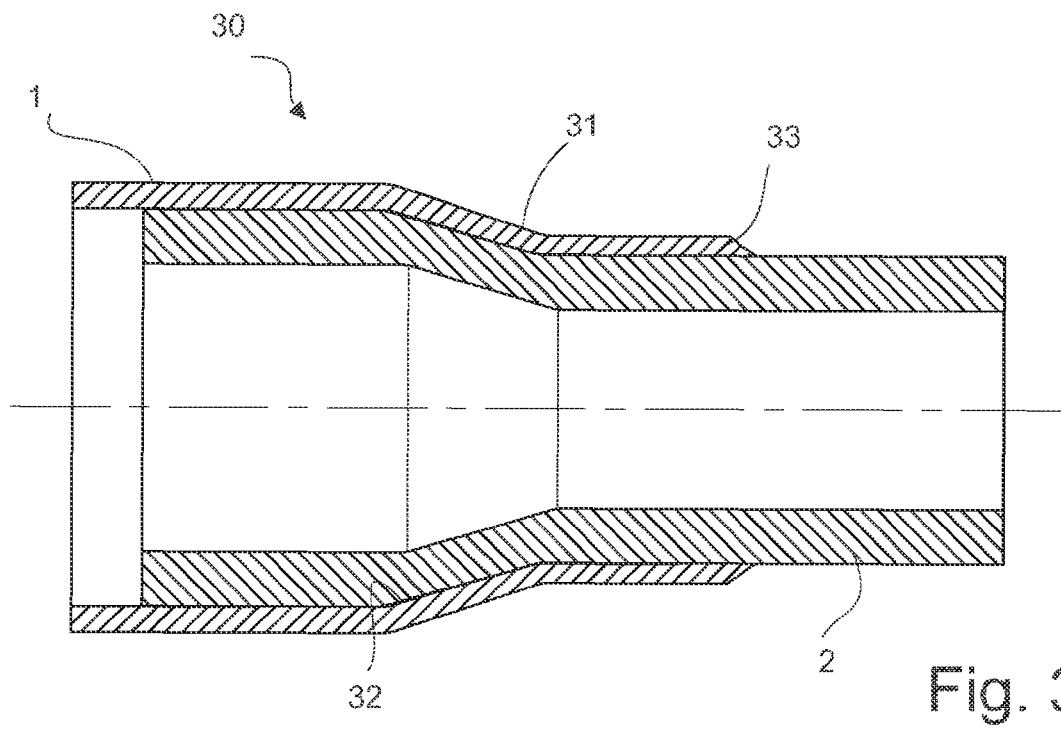
FIG. 3 shows a second embodiment of the catheter according to the invention seen in cross section along a longitudinal axis.

FIG. 3 shows the principle of another embodiment of a catheter 30 according to the invention. The distal section 1 (the outer section) displays a decreased outer circumference 31 in the transition, whereas the proximal section 2 (the inner section) displays an increased outer circumference 32 in the transition.

The proximal end of the distal section 33 is here cut to allow for a smooth transition point.

By adding cylindrical parts such as the decreased outer circumference 31 and the increased outer circumference 32 the surface of the transition sections is increased, thereby creating a larger area wherein the distal section and proximal section can couple together.

Figure 4:
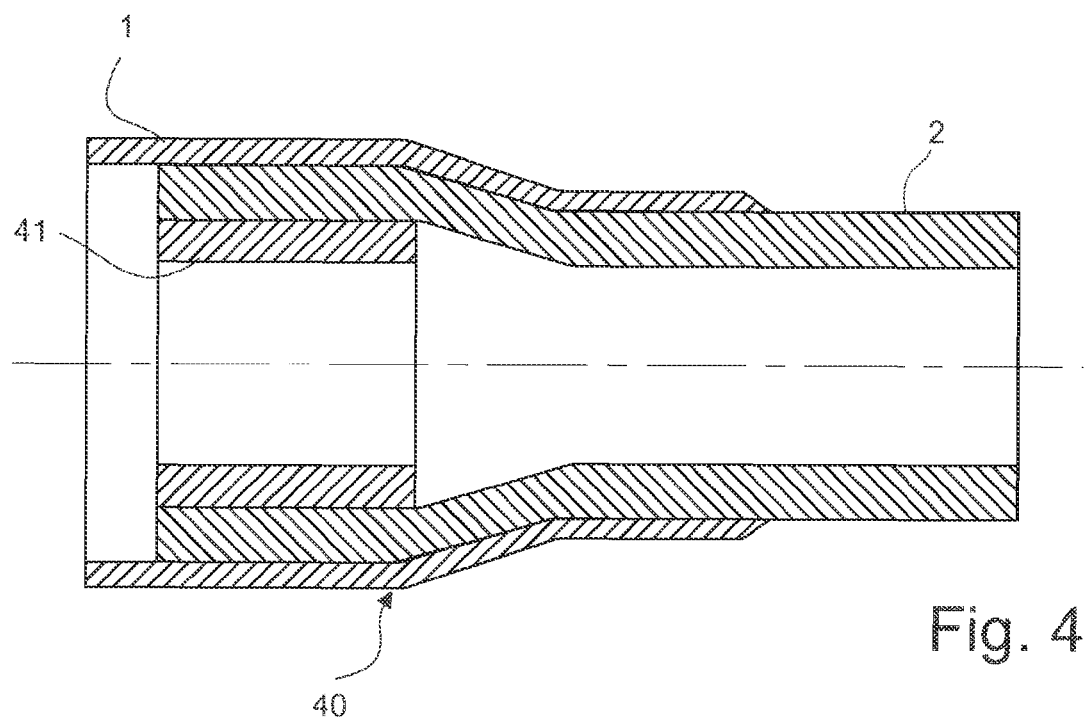
FIG. 4 shows a third embodiment of the catheter according to the invention seen in cross section along a longitudinal axis.

FIG. 4 shows another embodiment 40 of the catheter, which discloses one way to obtain decreased elasticity in the transition end (the distal end) of the proximal section.

The embodiment of FIG. 4 is identically to the embodiment of FIG. 3, however, the thickness of the wall has been doubled by insertion of an additional tube 41, which stabilizes the transition and provides decreased elasticity.

Figure 5:
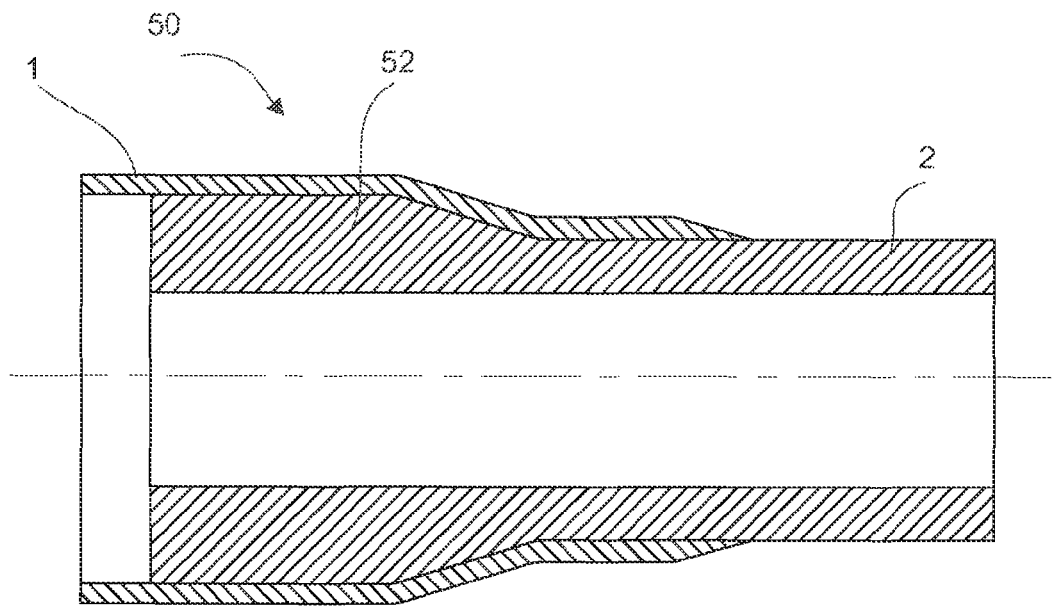
FIG. 5 shows a fourth embodiment of the catheter according to the invention seen in cross section along a longitudinal axis.

FIG. 5 shows another embodiment 50 of the catheter, which discloses one way to obtain decreased elasticity in the transition end (the distal end) of the proximal section. Here, the thickness of the end wall of the distal section 1 has been increased by molding the tube with a thicker wall 52.

Figure 6:
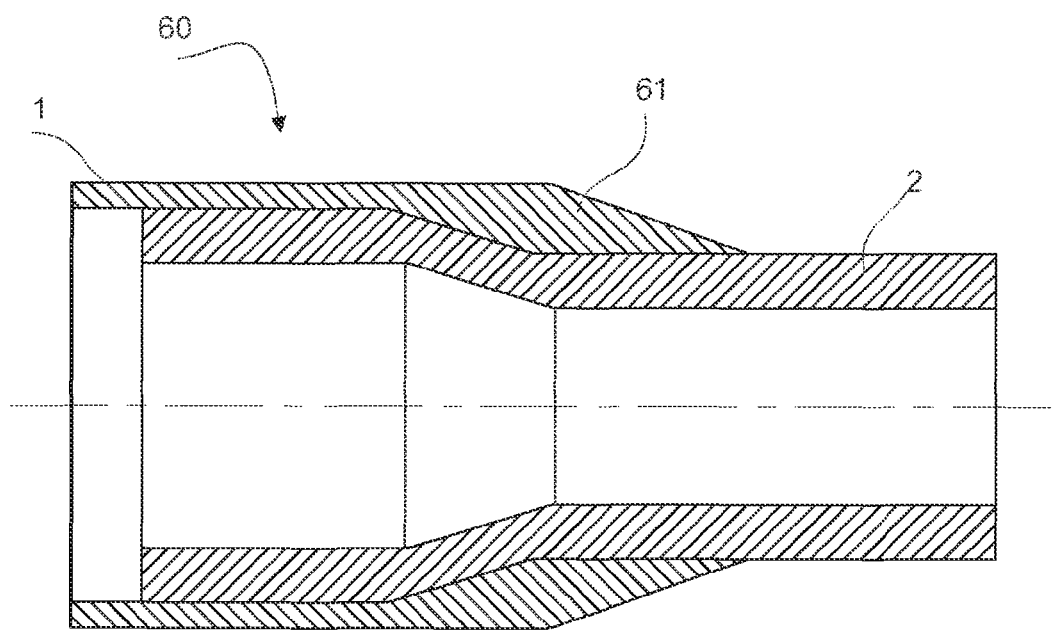
FIG. 6 shows a fifth embodiment of the catheter according to the invention seen in cross section along a longitudinal axis.

FIG. 6 shows another embodiment 60 of the catheter, which discloses one way to obtain decreased elasticity in the transition end (the proximal end) of the distal section. Here, the thickness of the end wall of the distal section 1 has been increased by molding the tube with a thicker wall 61 on that part.

Figure 7:
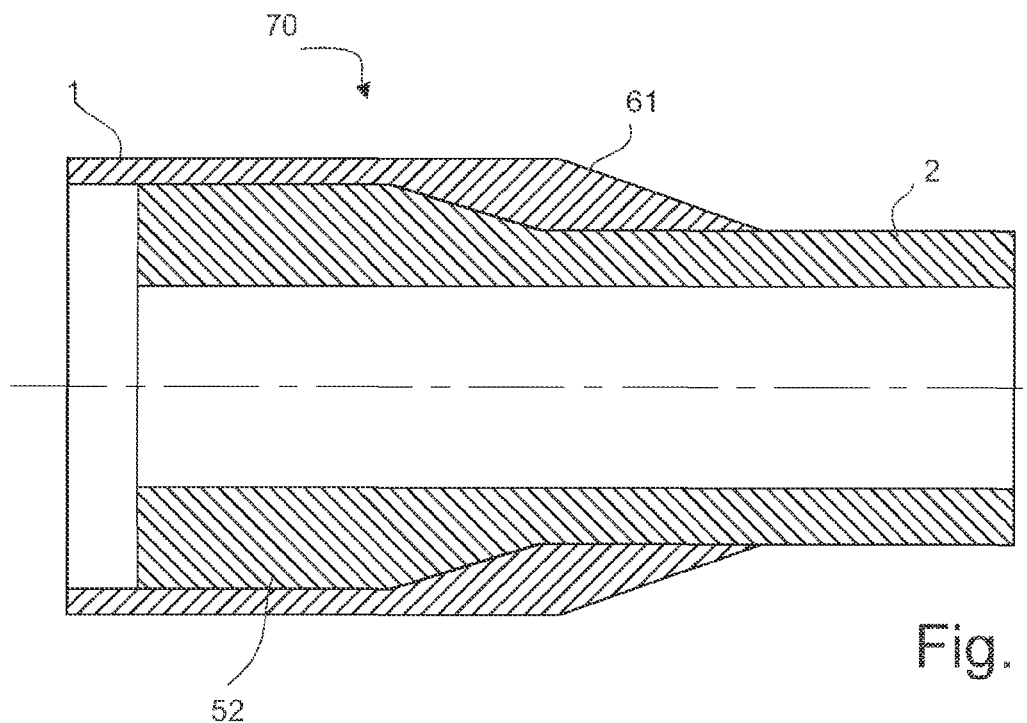
FIG. 7 shows a sixth embodiment of the catheter according to the invention seen in cross section along a longitudinal axis.

FIG. 7 shows another embodiment 70 of the catheter, which discloses a combination of FIG. 4 shows another embodiment 40 of the catheter, which discloses one way to obtain decreased elasticity in the transition end (the distal end) of the proximal section.

The embodiment of FIG. 4 is identically to the embodiment of FIG. 3, however, the thickness of the wall has been doubled by insertion of an additional tube 41, which stabilizes the transition and provides decreased elasticity.

and FIG. 5 shows another embodiment 50 of the catheter, which discloses one way to obtain decreased elasticity in the transition end (the distal end) of the proximal section. Here, the thickness of the end wall of the distal section 1 has been increased by molding the tube with a thicker wall 52.

: an increased wall-thickness in the transition end of both the distal section and the proximal section.

Figure 8:
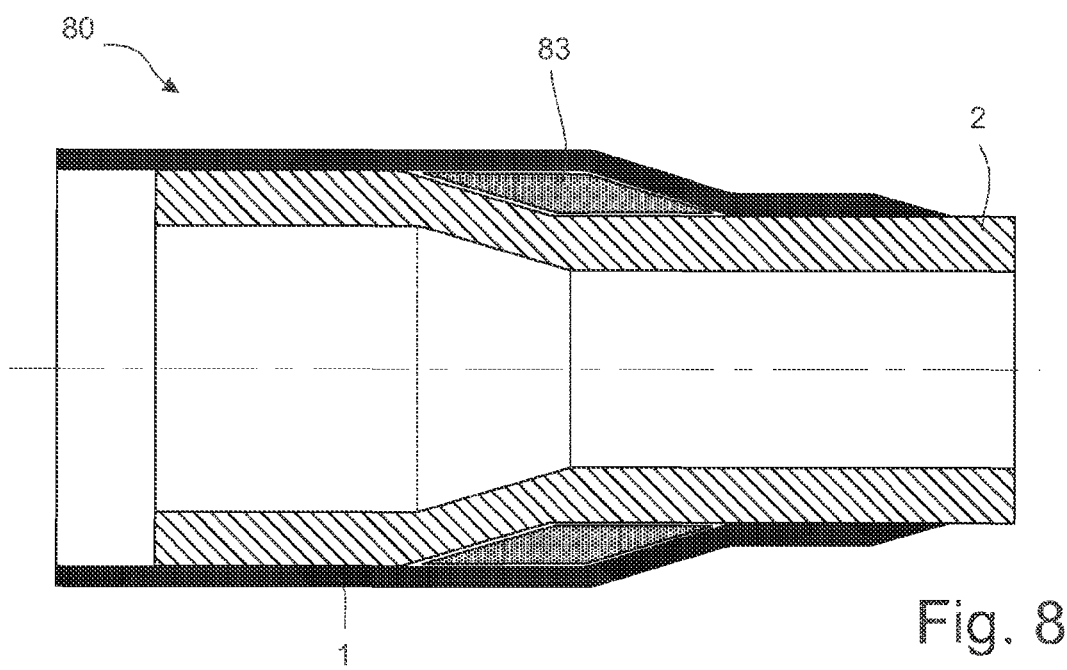
FIG. 8 shows a seventh embodiment of the catheter according to the invention seen in cross section along a longitudinal axis.

FIG. 8 shows another embodiment 80 of the catheter, which discloses transition with a third element. That is, the thick black line is the distal section 81. The outer circumference of the distal section decreases (going from left to right), is followed by a flat segment, and is thereafter pointed to provide for a smooth transition point. The proximal section 82 is the hatched line. The outer circumference of this proximal section increases (going from right to left). The two sections can be pulled together. However, a third element 83 is positioned between the decrease in outer circumference of the distal section and the increase in outer diameter of the proximal section.

Figure 9:
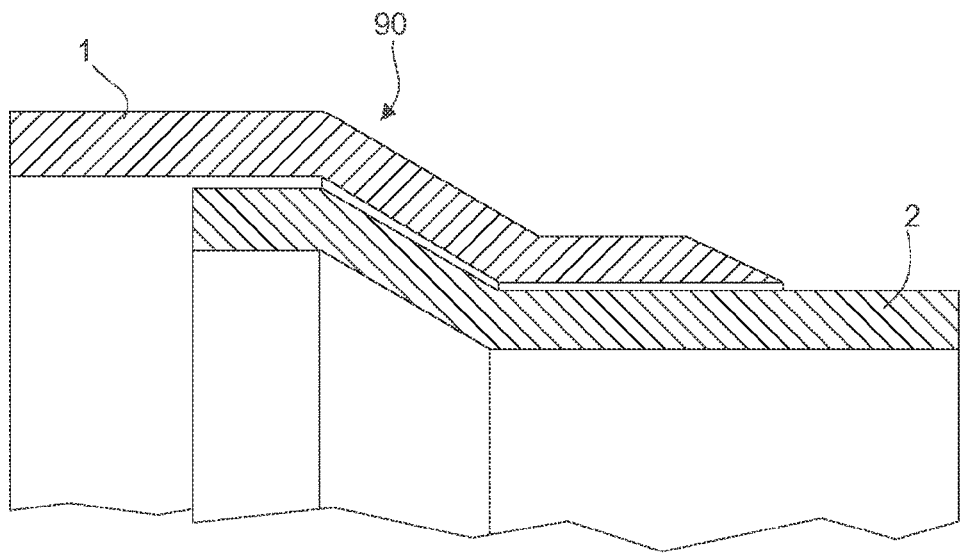
FIG. 9 shows seen in section an eighth embodiment of the catheter according to the invention.

FIG. 9 illustrates another embodiment 90 of the catheter and the transition between the distal section 1 (left) and the proximal section 2 (right). The distal section is cut to be pointed towards the end (the proximal end) and fits towards the regular tubular part of the proximal section.

Figure 10:
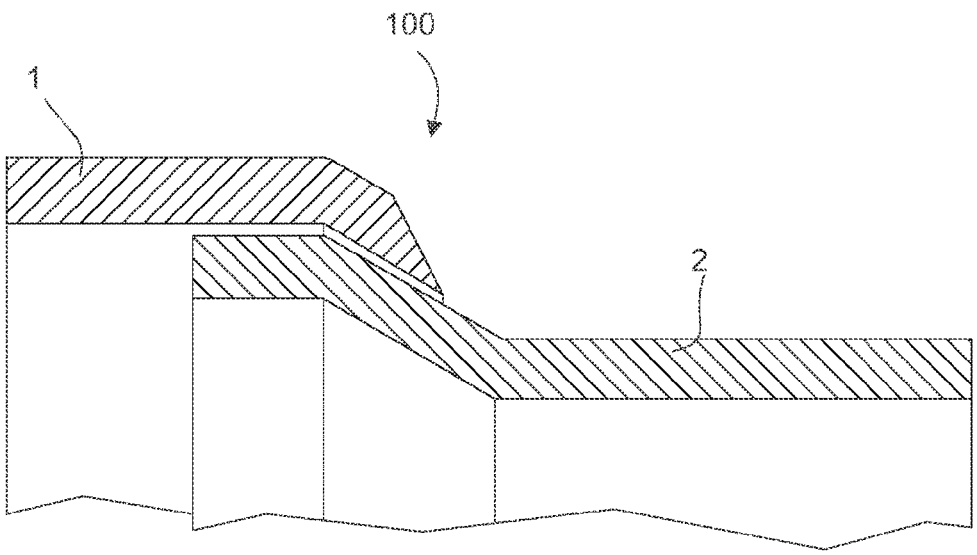
FIG. 10 shows seen in section a ninth embodiment of the catheter according to the invention.

FIG. 10 illustrates another embodiment 100 of the catheter, which discloses the transition between the distal section 101 (left) and the proximal section 102 (right). The distal section is cut to be pointed towards the end (the proximal end) and fits towards the part of the proximal section undergoing an increase in outer circumference. The inner circumference of the tip in the transition end of the distal part is bigger than the outer circumference of the proximal section so that a coating on the proximal section is not damaged when the tip passes this section during expansion of the catheter.

Figure 11:
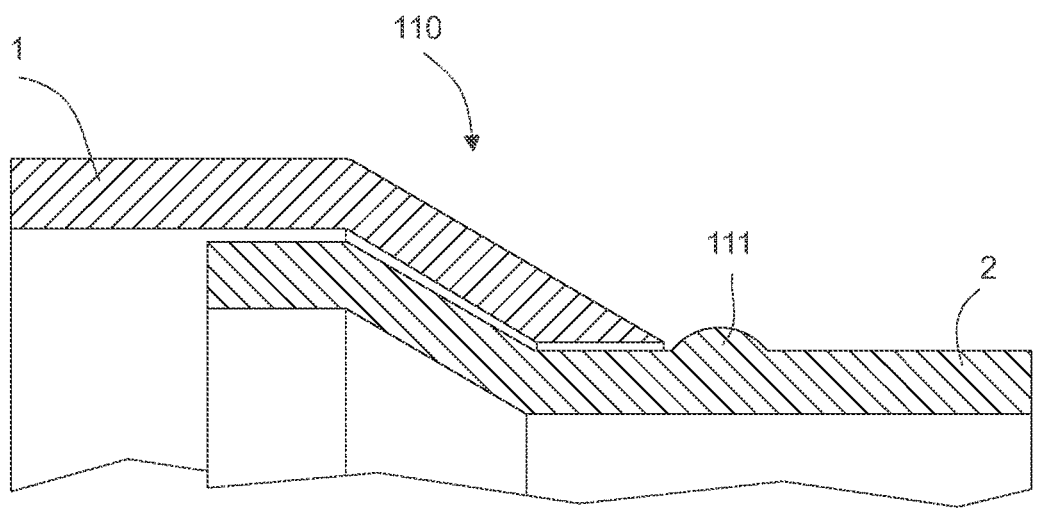
FIG. 11 shows seen in section a tenth embodiment of the catheter according to the invention.

FIG. 11 illustrates another embodiment 110 of the catheter, which discloses a bulb 111 on the proximal tube, just proximally to the transition part.

Figure 14:
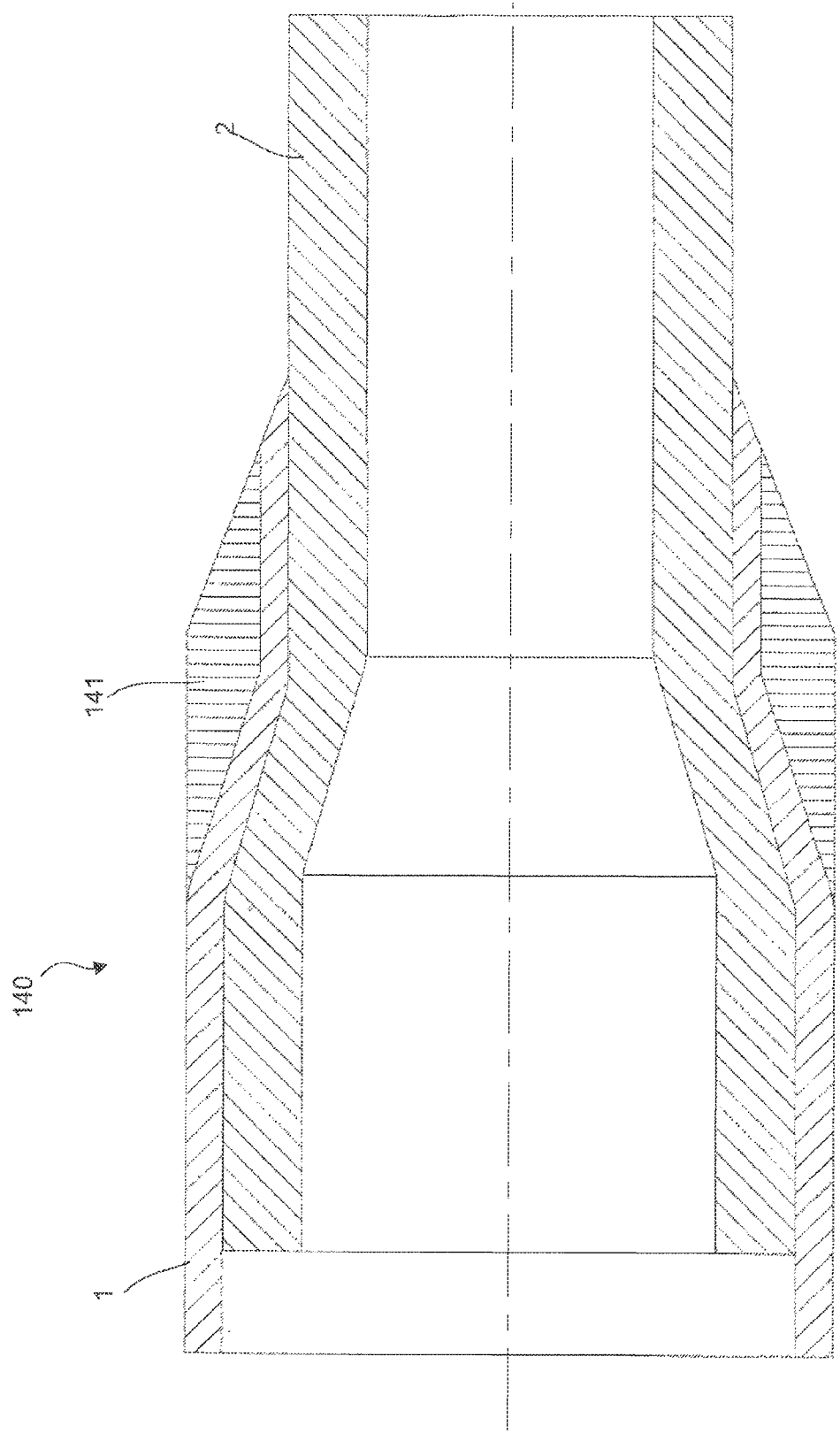
FIG. 14 shows an eleventh embodiment of the catheter according to the invention seen in cross section along a longitudinal axis.

FIG. 14 illustrates another embodiment 140 of the catheter according to the invention. Here a third element 141 is placed on the outside of the transition part of the distal section. The third element is formed as a ring having an outer circumference of the same size as the outer circumference of the distal section. The third element has a proximal face which tapers with the same angle as the proximal end of the distal section.

FIG. 15 illustrates the forces between the distal section 1 and the proximal section as described earlier when the catheter is in its expanded configuration. The sections are only shown schematically and solid lines indicate their walls. The area between the tapering part of the two sections defines the conical contact zone 150.

Although dry catheters are easier to engage in a frictional lock with each other, a hydrophilic catheter may also engage into a frictional lock when first and second conical faces 151,152 of the two sections are pulled against each other in the contact zone 150. High friction may thus be provided when a first angle $\alpha_1$ of the first conical face 151 (relative to the axis of the distal section) and a second angle $\alpha_2$ of the second conical face 152 (relative to the axis of the proximal section) are less than 40°.

Low friction is created when the first angle $\alpha_1$ and the second angle $\alpha_2$ are between 90° and 110°.

Figure 18:
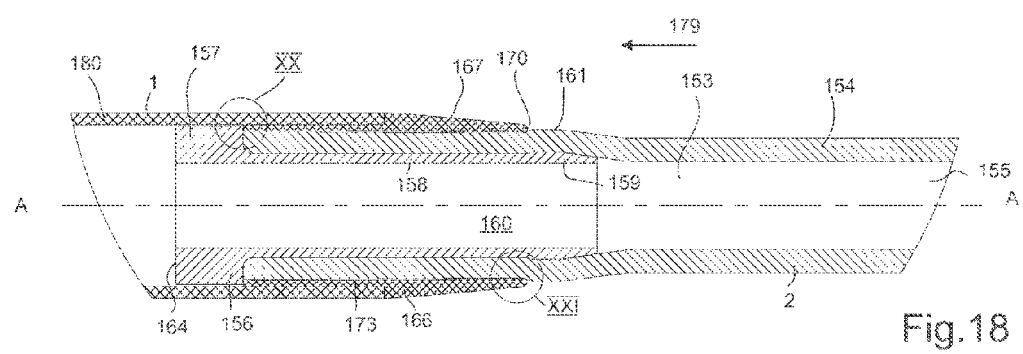
FIG. 16-21 shows a twelfth embodiment of the catheter according to the invention.
Figure 17:
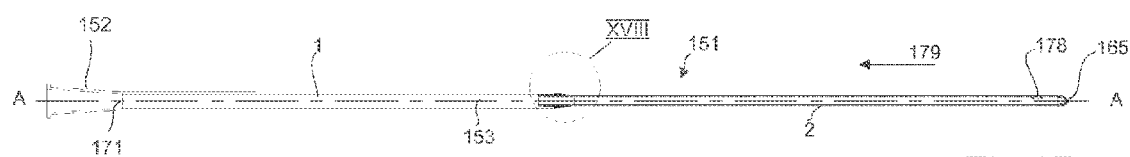
Figure 21:
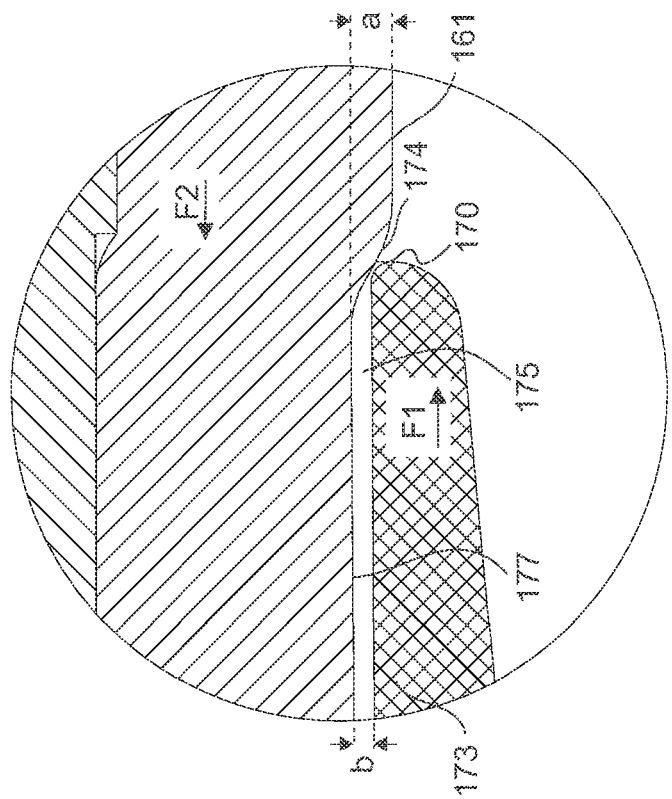
Figure 20:
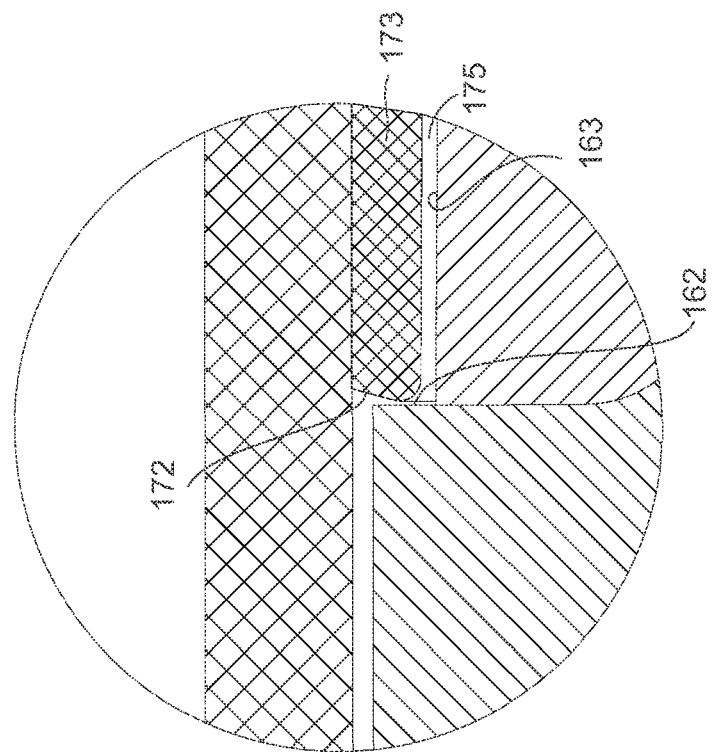

FIGS. 16-21 shows one embodiment of an expandable catheter 151. FIG. 18 shows an enlarged view of section XVIII in FIG. 17 and FIGS. 20 and 21 shows enlarged views of sections XX and XXI, respectively, in FIG. 18. FIGS. 19a and 19b shows respectively a distal section and a proximal section of FIG. 18. The sections illustrated in FIGS. 19a and 19b are shown in an exploded view along axis A-A.

Figure 16:
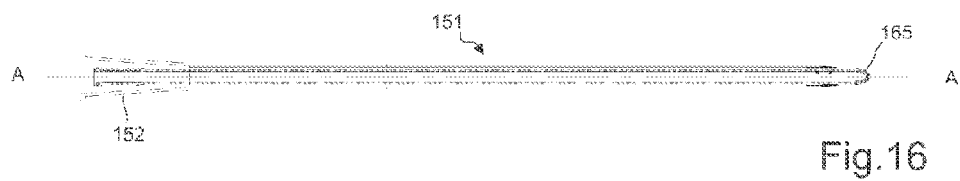
Figure 19A:
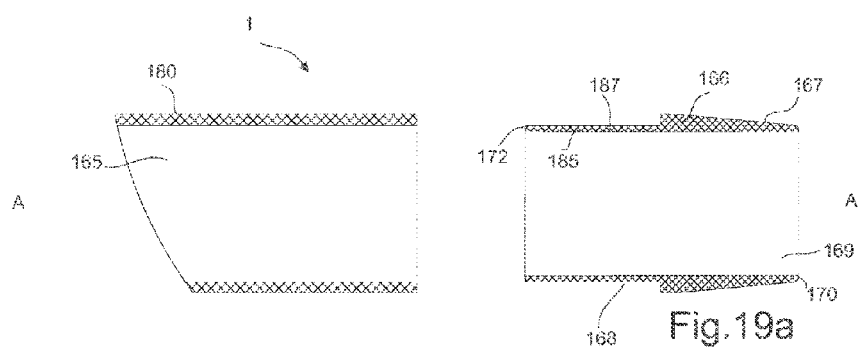
Figure 19B:
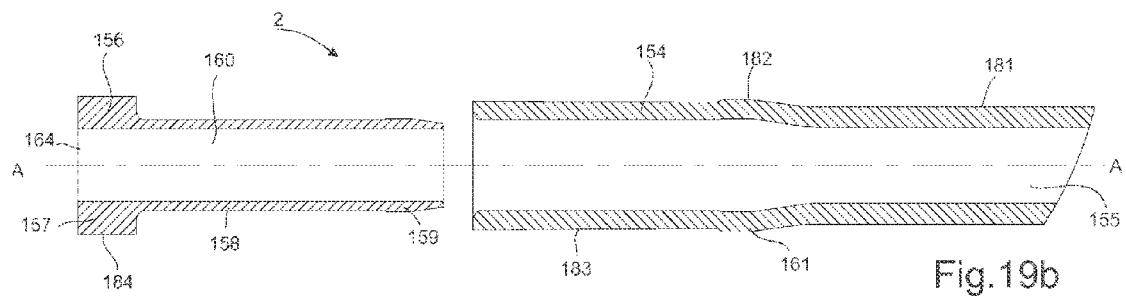

The catheter 151 is operable between a collapsed configuration, shown in FIG. 16, for storage and transportation and an expanded configuration, shown in FIG. 17, for draining fluid from a body via a conduit 153 which extends axially in a longitudinal direction, indicated by arrow 179, from a proximal end 165 to an opposite distal end 171.

The catheter comprises a proximal section 2, adapted to be fully inserted into a urinary channel of the body (not shown) and forming a proximal part of the conduit which part extends axially between the proximal end 165 and a first transition end 164 of the proximal section 2.

The catheter further comprises a distal section 1, adapted to be at least partially inserted into the urinary channel (not shown) and forming a distal part of the conduit which part extends axially between a second transition end 170 of the distal section 1 and the distal end 171.

The first transition end 164 is dimensioned to enable its positioning inside a receiving portion of the distal part of the conduit 153 to enable axial movement of the sections relative to each other to operate the catheter 151 between the collapsed configuration and the expanded configuration of the catheter, wherein the sections comprise cooperating coupling structures to support the catheter in the expanded configuration.

Beside the proximal section 2 and the distal section 1, the catheter 151 is also provided with a connector 152. Together the two sections and the connector forms the conduit 153 extending axially along the axis A-A.

The proximal section is formed of a proximal catheter tube 154, defining a first duct 155, and a first sleeve 156 having a base 157, a shaft 158, a head 159 and a second duct 160 extending there through. The first transition end 164 and the proximal end 165 define the axial extent of the proximal section.

The head and the shaft of the first sleeve are inserted into the first duct of the proximal catheter tube and thereby form the proximal section. In this configuration the first duct and the second duct together defines a proximal part of the conduit. To avoid separation the proximal catheter tube and the first sleeve are welded together. Other means for joining exists, such as gluing. Additionally or alternatively the outer circumference of the shaft and the head of the first sleeve may be larger than the inner circumference of the proximal catheter tube whereby the tube will grip tightly around the first sleeve.

As can be seen the first proximal section have an outer surface with a first surface portion 181 with a first circumference, which when seen in the longitudinal direction is followed by a second surface 182 having a second circumference which is larger than the first circumference. A third surface portion 183 follows the second surface portion. The third circumference of the third surface portion is smaller than the second surface portion. By providing smooth transitions between the first, second and third surface portion a bulb 161 is provided on the outer surface of the proximal catheter tube. In practice the bulb 161 is provided by the head 159, which is formed with an enlarged surface portion, which has a larger circumference than the shaft 158. The head will thereby radially expand the proximal catheter tube and create the bulb 161.

By forming a fourth surface portion 184 on the base 157 with a circumference which is larger than the circumference of the third surface portion, a first rim 162 is provided when the proximal catheter tube and the first sleeve are joined to form the proximal section. A slot 163 is thereby formed between the second surface portion, i.e. the bulb 161, and the fourth surface portion, i.e. the first rim 162.

The distal section 1 is formed of a distal catheter tube 180, defining a third duct 165 and a second sleeve 166 having an outer tapering surface 167, an incision 168 and a fourth duct 169. A second transition end 170 and a distal end 171 define the axial extent of the proximal section.

The circumference of the fourth duct of the second sleeve is smaller than the circumference of the third duct of the distal catheter tube. When they are joined this relation provides a second rim 172. A key 173, provided by a fifth surface portion 185, is thus defined between the second rim and the second transition end 170.

In order to provide as smooth transition to from the proximal section to the distal section when the catheter is in its expanded configuration the outer surface of the second sleeve has an eighth surface portion shown as the outer tapering surface 167, which decreases towards the second transition end.

The distal catheter tube 180 and the second sleeve 166 are joined together by inserting the incision into the third duct. The area of the distal catheter tube contacting a ninth surface portion 187 of the incision thereto is then welded together to fix the distal catheter tube and the second sleeve to each other. In this configuration the third duct and fourth duct together forms the distal part of the conduit.

When the catheter is moved from its collapsed configuration, as shown in FIG. 16, to its expanded configuration, as shown in FIG. 17, the key 173 engages with the slot 163 and thereby couples the proximal section and the distal together in the expanded configuration.

The illustrated catheter assembly is especially advantageous for use with expandable catheters having a hydrophilic coating (not shown). As can especially be seen in FIGS. 20 and 21 a gap 175 is provided between the surface of the key and the surface of the slot. A gap of approximately the same size is furthermore provided when the key is displaced along the first surface portion 181 of the proximal section on the other side of the bulb 161 from the slot. The gap provides radial clearance between the key and the first surface portion which avoids that the hydrophilic coating is scraped off the proximal section when the sections are axially displaced. Furthermore, the hydrophilic coating will fill out the gap and the surface tension of the hydrophilic coating will advantageously center the key evenly around the first surface portion.

As can be seen the axial extent of the key is slightly longer than the extent of the slot. This will jam the key between the first rim and the sloping surface 174 of the bulb 161. Advantageously this will seal off the gap whereby the mucosa of the urethra, which is very flexible, i.e. the mucosa follows the curvature of the urinary catheter, may be prevented to enter the gap wherein the mucosa otherwise could get caught between the key and slot and consequently get squeezed causing pain and maybe even tear the mucosa.

As the circumference of the key 173 limits the outer circumference of the proximal catheter tube the key typically only extends a few millimeters. Thus, to provide secure engagement of the proximal and distal section and to avoid that they unintentionally are pulled apart it is desirable that the first rim 162 and the second rim 172 contacts each other in a large surface area. Furthermore it is desirable that the edges of the first and second rim and are well defined, and preferably has a small rounding in order to prevent that the rounding surface may act as guides which may push the rims key over the fourth surface portion 184.

In order to properly seal the gap the second transition end 170, which abuts against the bulb 161 is exerting an axially directed force $F_1$ onto the distal sloping surface 174 of the bulb. For secure seal the sloping surface will react with an equally opposite axially directed force $F_2$. However should the size of the force $F_1$ become too large the bulb will collapse, which will result in that the distal and proximal section will be uncoupled and the catheter will move from its expanded configuration to its collapsed configuration.

In order to prevent this the distance between the radial extending distance from the surface 177 of the slot to the maximal radial extending distance of the bulb, a, should be at least two times the length than the radial extending distance from the surface of the slot to the surface of the key, b, i.e. a≥2*b. The distance b corresponds to the size of the gap 175 seen transverse to the longitudinal direction. It should however be understood that this relation may vary depending on the material of respectively the key and the bulb and the type of coating used to coat the catheter.

Furthermore, the angular slope of the distal sloping surface 174 to the axis A-A will affect the required size of $F_1$ in order for the sections to uncouple and the chance that the mucosa may get squeezed between the second transition end and the sloping surface. Furthermore such relations will also depend on the types of materials used.

One type of materials used to produce the catheter may be rigid polyurethane, such as Estane ETE X1014 for the distal section 1 and the first sleeve 156. The proximal catheter tube 154 may for example be formed of soft polyurethane, such as Estane 58212.

When used the expandable catheter is moved from its collapsed configuration into its expanded configuration. The proximal end 165 is inserted into the urethra followed by the proximal section 2 and the distal section 3 until urine start flowing through the conduit.

The catheter is usually inserted by into the urethra by gripping the connector part 152 between two or more fingers of one hand and guiding the proximal end into the urethra with the other hand. The urine will flow through the through a hole 178 formed in the proximal section 2 close to the proximal end, into the conduit and then through the conduit in mainly a longitudinal direction parallel to the longitudinal extent, shown as axis A-A in FIGS. 17-19b, of the conduit, as indicated by the arrow 179 in FIGS. 15 and 16, and out through the connector 152.

Although the embodiment illustrated in FIGS. 15a-18 is especially suited for hydrophilic-coated catheters it may be used for other types of coated catheters known to the skilled person, for example gel coated catheters.

Figure 22:
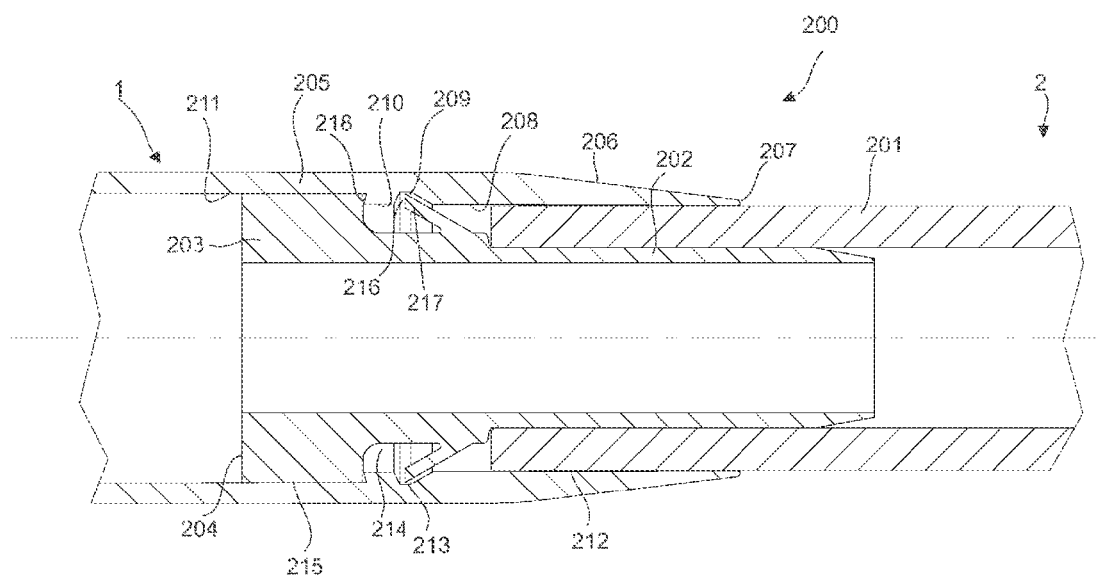
FIG. 22 shows a thirteenth embodiment of the catheter according to the invention seen in cross section along a longitudinal axis.

FIG. 22 illustrates another embodiment of the coupling structures of a catheter 200 according to invention. The figure shows seen in longitudinal section the area of the catheter in where the proximal section 2 and the distal section 1 couples together in the catheters expanded configuration.

The proximal section is formed of a proximal catheter tube 201 wherein the neck 202 of a sleeve 203 is inserted. In order to fix the two parts together a weld has been provided between the neck and the inner surface of the proximal catheter tube. A first transition end 204 is defined at the distal end of the sleeve 203

The distal section is formed of a one-piece molded catheter tube 205. The distal section have a first outer surface portion 206 having an increasing circumference seen from a second transition end in the longitudinal direction towards a distal end (not shown). The inner surface of the distal section is, seen in order from the second transition end, provided with a first 208, second 209, third 210 and fourth 211 surface portions. The first and third surface portions have a smaller circumference than the second and fourth surface portion. As can be seen in FIG. 22 the second surface portion thus forms a slot 216 defined by the first and third surface portion.

Corresponding to the inner surface portions of the distal section there is provided a fifth 212, sixth 213, seventh 214 and eighth 215 surface portions on the outer surface of the proximal part. The fifth surface portion has a circumference, which is smaller than the circumference of the first surface portion, and the seventh surface portion has a circumference, which is smaller than the circumference of the third surface portion. The sixth surface portion has a circumference, which is smaller than the second surface portion but larger than the circumference of the fifth and seventh surface portion. The eighth surface portion has a circumference which is smaller than the circumference of the fourth surface portion but larger than the circumference of the third surface portion.

The sixth surface portion is advantageously provided as an annular flange being flexible transverse to the axis of the catheter. This allows for the flange to function as a key 217, which engages with the slot when the catheter is in its expanded configuration. By being flexible the key will easily move past the third surface portion.

Furthermore, as the eighth surface portion has a circumference which is larger than the circumference of the third surface portion a stop is provided as a protruding rim 218, which prevents the distal section and the proximal section from being pulled apart.

EXAMPLES

Example 1

Pull-Out Force Endurance

The test is performed as a tensile test in a standard test machine as a Lloyd LR 5K. The desired konical connection is placed in the tensile test machine and the force is measured when the parts are pulled apart. The maximum load is registered. Materials in the test is Estane ETE X1014 for the outer tube and Estane 58212 for the inner tube (see Table 1).

Figure 2:
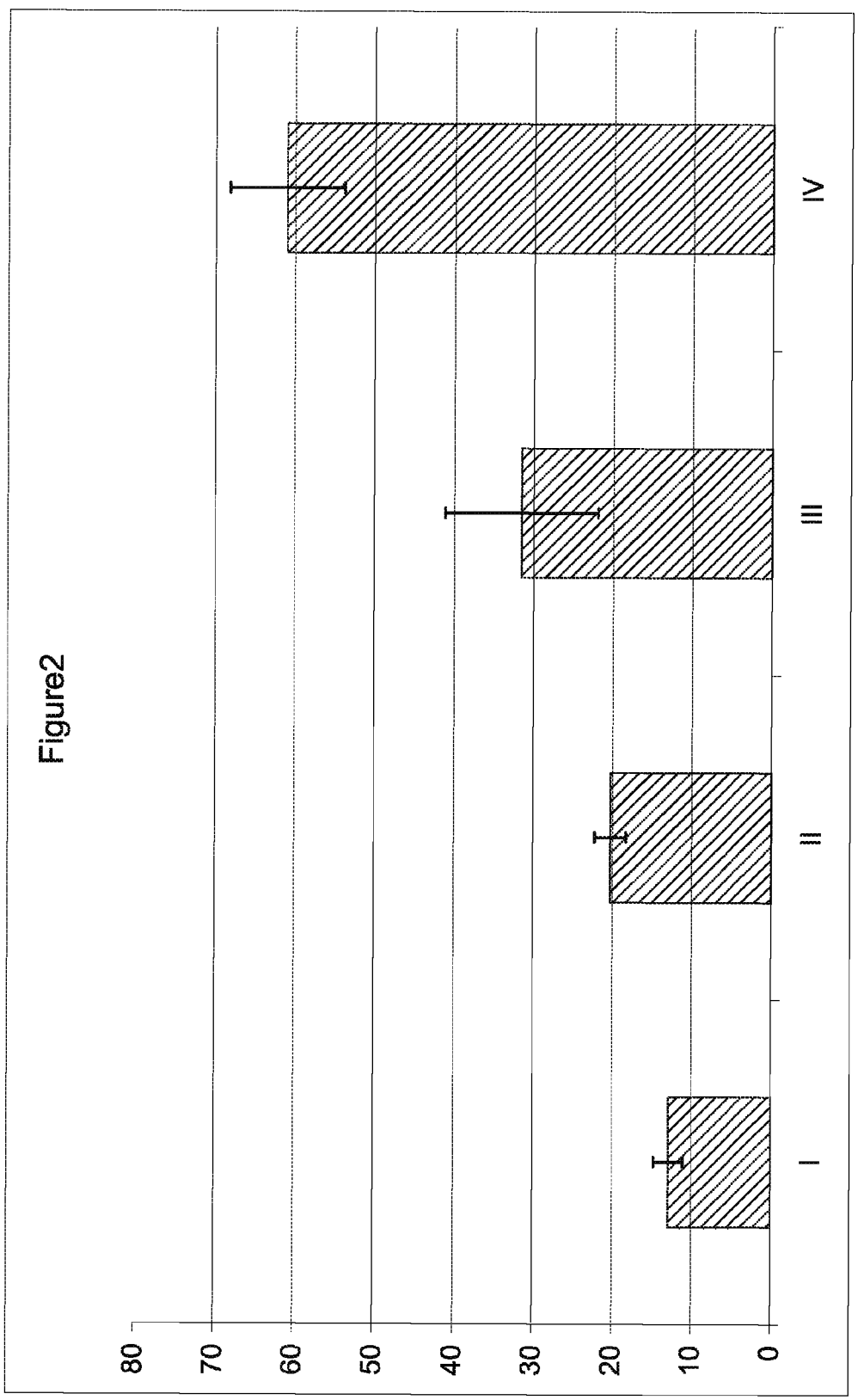
FIG. 2 shows a chart indicating the force required to pull apart to conically shaped transition sections and where the ordinate axis indicates max load [N]

The default configuration takes about 12 N to pull apart ( FIG. 2, I). However, when the thickness of the distal section is doubled (for example to 0,7 mm) it takes about 20N to pull the two sections apart (FIG. 2, II. FIG. 5 shows another embodiment 50 of the catheter, which discloses one way to obtain decreased elasticity in the transition end (the distal end) of the proximal section. Here, the thickness of the end wall of the distal section 1 has been increased by molding the tube with a thicker wall 52.

If the thickness of the wall of the proximal section is increased to 1.6 mm, the force required to pull the two sections apart goes from 12 N to about 30 N ( FIG. 2, III. FIG. 3 shows the principle of another embodiment of a catheter 30 according to the invention. The distal section 1 (the outer section) displays a decreased outer circumference 31 in the transition, whereas the proximal section 2 (the inner section) displays an increased outer circumference 32 in the transition.

The proximal end of the distal section 33 is here cut to allow for a smooth transition point.

By adding cylindrical parts such as the decreased outer circumference 31 and the increased outer circumference 32 the surface of the transition sections is increased, thereby creating a larger area wherein the distal section and proximal section can couple together.)

A synergistic effect was observed when the thickness of both the proximal and the distal transition was increased (doubled as described above). Then, a force of about 60 N was required to pull the sections apart (FIG. 2, IV, FIG. 6 shows another embodiment 60 of the catheter, which discloses one way to obtain decreased elasticity in the transition end (the proximal end) of the distal section. Here, the thickness of the end wall of the distal section 1 has been increased by molding the tube with a thicker wall 61 on that part).

Example 2

Catheter with Increased Wall Thickness

In this example, sufficient endurance of the transition between the proximal section and the distal section in an expanded catheter is obtained by increasing the wall thickness.

As clearly shown in FIG. 3 shows the principle of another embodiment of a catheter 30 according to the invention. The distal section 1 (the outer section) displays a decreased outer circumference 31 in the transition, whereas the proximal section 2 (the inner section) displays an increased outer circumference 32 in the transition.

The proximal end of the distal section 33 is here cut to allow for a smooth transition point.

By adding cylindrical parts such as the decreased outer circumference 31 and the increased outer circumference 32 the surface of the transition sections is increased, thereby creating a larger area wherein the distal section and proximal section can couple together.

A doubling of the wall thickness is obtained by inserting an additional tube inside the proximal tube (in the distal end, the transition end).

However, during molding of the catheter tube, the inner-wall can be reinforced by increasing the wall-thickness—such increased wall-thickness is clearly illustrated in FIG. 4 shows another embodiment 40 of the catheter, which discloses one way to obtain decreased elasticity in the transition end (the distal end) of the proximal section.

The embodiment of FIG. 4 is identically to the embodiment of FIG. 3, however, the thickness of the wall has been doubled by insertion of an additional tube 41, which stabilizes the transition and provides decreased elasticity.

The same principle as described for the inner-wall, can be applied to the outer-wall (the distal section). As shown in FIG. 5 shows another embodiment 50 of the catheter, which discloses one way to obtain decreased elasticity in the transition end (the distal end) of the proximal section. Here, the thickness of the end wall of the distal section 1 has been increased by molding the tube with a thicker wall 52.

The thickness of the wall of the distal section is increased while the inner circumference of the tube is decreased. From the outside it appears as a straight line, giving a smooth feeling to this reinforcement. When the outer circumference of the proximal section has reached its minimum (that is, the circumference the rest of the tube has) the decrease in outer circumference of the distal section starts, ending in a smooth transition.

However, to obtain the highest pull-force, as disclosed in the example above, a combination of decreased elasticity of both the inner- and outer tubes is provided in the transition, only. Such combination is illustrated in FIG. 6 shows another embodiment 60 of the catheter, which discloses one way to obtain decreased elasticity in the transition end (the proximal end) of the distal section. Here, the thickness of the end wall of the distal section 1 has been increased by molding the tube with a thicker wall 61 on that part.

In one embodiment, the wall thickness of the distal section increases while the inner circumference of the tube decreases. The decrease in inner circumference of this distal section is matched with an increase in outer circumference of the proximal section. However, during this increase in outer circumference of the proximal section the inner circumference is kept constant. Hereby, both of the sections comprise reinforced transition parts.

Example 3

Catheter with Third Element

As illustrated in FIG. 7 shows another embodiment 70 of the catheter, which discloses a combination of FIG. 4 shows another embodiment 40 of the catheter, which discloses one way to obtain decreased elasticity in the transition end (the distal end) of the proximal section.

The embodiment of FIG. 4 is identically to the embodiment of FIG. 3, however, the thickness of the wall has been doubled by insertion of an additional tube 41, which stabilizes the transition and provides decreased elasticity.

FIG. 5 shows another embodiment 50 of the catheter, which discloses one way to obtain decreased elasticity in the transition end (the distal end) of the proximal section. Here, the thickness of the end wall of the distal section 1 has been increased by molding the tube with a thicker wall 52.

FIG. 5 shows an increased wall-thickness in the transition end of both the distal section and the proximal section.

The decreased elasticity in the transition can effectively be provided to both sections through a third element. This element will become trapped between the two sections, and provide the endurance needed. An example is a third element made of ESTANE X4995 thermoplastic elastomer. In this case, both sections shall endure full expansion/compression in order to separate. Here, the material is placed between the two sections (FIG. 8). However, as illustrated in FIG. 14, this third material can be placed on the outside of the tubes as well.

Example 4

Transition Point

It is important to provide a smooth transition point. Especially, the actual point of transition, that is where mucosal exposure to the proximal section stops and mucosal exposure to the section begins. As illustrated in FIG. 8 shows another embodiment 80 of the catheter, which discloses transition with a third element. That is, the thick black line is the distal section 81. The outer circumference of the distal section decreases (going from left to right), is followed by a flat segment, and is thereafter pointed to provide for a smooth transition point. The proximal section 82 is the hatched line. The outer circumference of this proximal section increases (going from right to left). The two sections can be pulled together. However, a third element 83 is positioned between the decrease in outer circumference of the distal section and the increase in outer diameter of the proximal section.

One such transition can be obtained by cutting the proximal end of the distal section in a pointed angle. However, as illustrated in FIG. 9, this pointed angle can fit closely to the segment of the proximal section where the outer diameter is increasing. Obtained hereby is that the outer diameter of the regular tubular segment of the proximal section is smaller than the inner diameter of the proximal end of the distal section. The coating of the catheter is not damaged during pulling the two sections together during expansion of the catheter.

An alternative is illustrated in FIG. 10 illustrates another embodiment 100 of the catheter, which discloses the transition between the distal section 101 (left) and the proximal section 102 (right). The distal section is cut to be pointed towards the end (the proximal end) and fits towards the part of the proximal section undergoing an increase in outer circumference. The inner circumference of the tip in the transition end of the distal part is bigger than the outer circumference of the proximal section so that a coating on the proximal section is not damaged when the tip passes this section during expansion of the catheter.

FIG. 11 illustrates another embodiment 110 of the catheter, which discloses a bulb 111 on the proximal tube, just proximally to the transition part.

. Here, a bulb, or a circular protrusion is provided on the proximal section. This bulb will 'lift' the mucosa to avoid contact with the point of transition. Furthermore, such bulb will act as a mechanical lock between the distal and the proximal section of the catheter allowing passage in one direction but not in the other.

Example 5

Rigidity of Catheter Parts

The rigidity of a tube is a function of the design (form and circumference) and material properties such as E-modulus or for very soft materials the hardness. For a male person it is important that the proximal part of the catheter—the part that when inserted protrudes from the bladder to the pelvic floor—is soft and flexible in order to fit the curvature of the urethra. The rigidity must be low. At the same time the proximal part must have good kinkability.

In the contrary hereto, the distal part should be more rigid to enable easy insertion by avoiding that the catheter bends before the opening of the urethra (meatus). The kinkability of the distal part is typically not critical as it can be controlled and monitored by the user.

Estane ETE X1014 is the preferred material for the distal part and Estane 58212 is the preferred material for the proximal part. ETE 60DT3 is an example of material for the distal part with the lowest acceptable E-modulus—see Table 1 for data for different materials are mentioned.

A length of 11 cm is cut from the middle of the catheter. The catheter is placed in water at a temperature of 23° C. for 30 sec. The catheter is then placed in an adapter situated on the tensile test machine. The tensile machine is started and the force to compress the catheter is logged.

Figure 12:
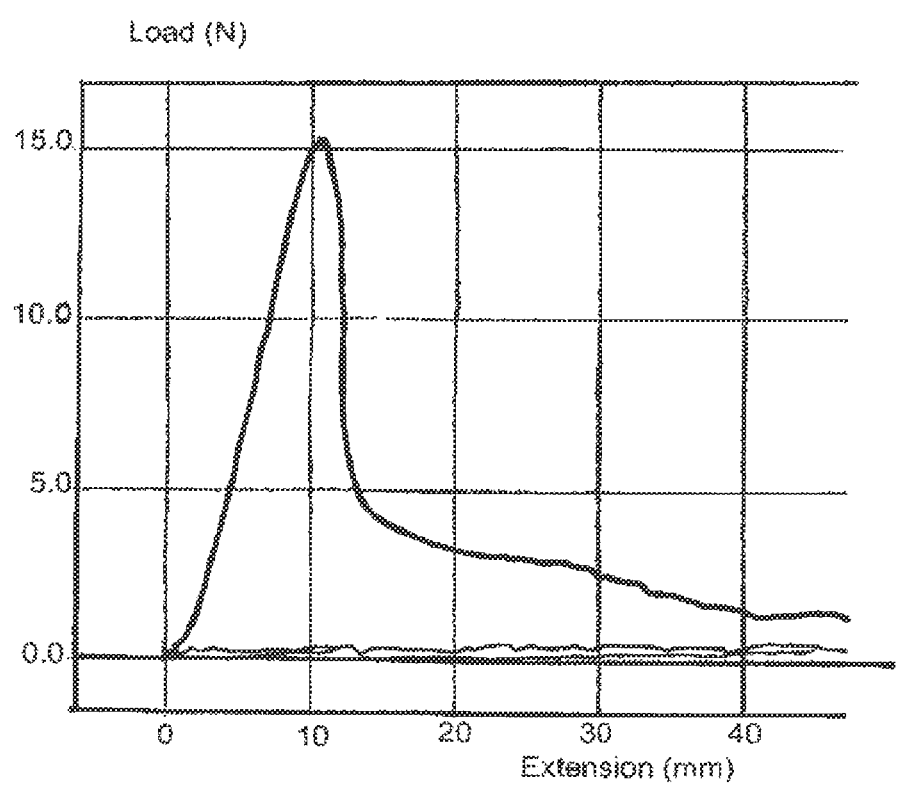
FIG. 12 shows a chart of the results of a tensile test performed on a distal section of a catheter according to the invention.

FIG. 12 shows the force applied to a typical distal catheter section. The abscissa indicates the compression of the section in millimeters (Extension, mm) and the ordinate indicates the load force applied in N.

As illustrated in FIG. 12, compression of this typical distal section with a high E-modulus results in a linear compression with the force applied. However, at a certain point (15 N), the section kinks, and the force needed for further bending is low.

Figure 13:
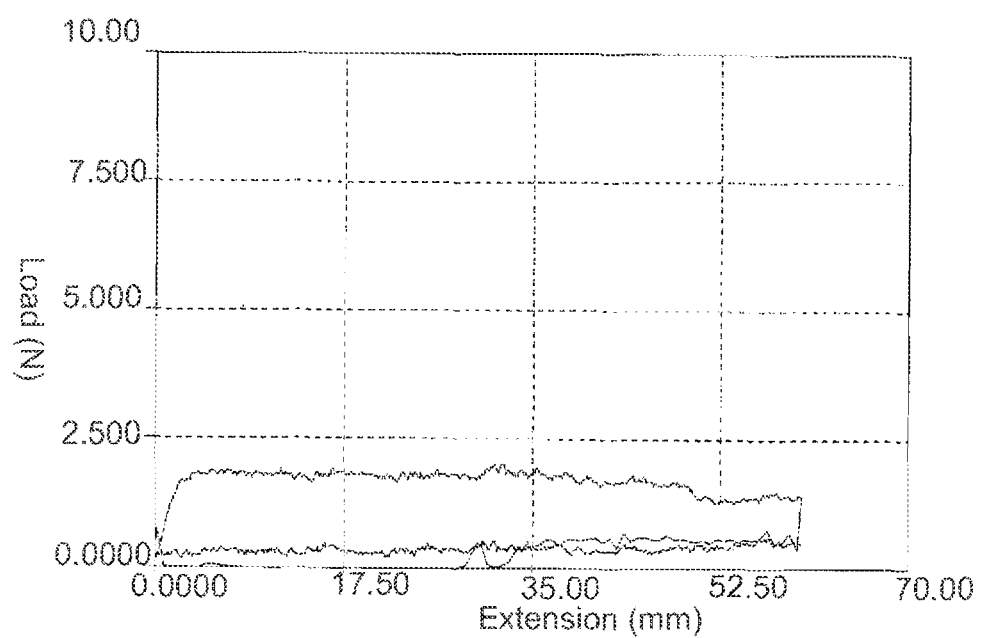
FIG. 13 shows a chart of the results of a tensile test performed on a proximal section of a catheter according to the invention.

FIG. 13 shows the force applied to a typical proximal catheter section as described. This elastic section will bend almost proportionally with the force applied. The abscissa indicates the compression of the section millimeters (Extension, mm) and the ordinate indicates the load force applied in N.

As illustrated in FIG. 13, compression of this typical proximal section with a low E-modulus results in a constant bending of the section with a constant force. The curve in FIG. 13 rises steeply from 0 to 2 N during the first four millimeters of compression of the proximal catheter section. After the first four millimeters the curve flattens, indicating that the proximal section has bent as it still exerts a load of approximately 2 N.

Thus, to provide a distal section and a proximal section so that the first longitudinal directed force required for moving the catheter from an expanded position to a collapsed position is larger than the second longitudinal directed force required for at least one of the proximal section and the distal section to bend, the first longitudinal directed force is chosen to be above 2 N, which is the second longitudinal directed force. I.e. the coupling structures provided when the catheter is in its expanded configuration needs to be rigid enough to resist a load of at least 2 N. Preferably the coupling configuration is dimensioned so that it may resist even higher loads, such as 3-10 N.

Alternatively, keeping in mind that the push-in force required to insert the catheter into the urethra is approximately 1 N, the proximal and distal sections can be provided so that the first longitudinal directed force required for moving the catheter from an expanded position to a collapsed position is smaller than the second longitudinal directed force required for at least one of the proximal section and the distal section to bend, wherein the coupling structures are dimensioned so that the first longitudinal force required is between 1 and 2 N, especially between 1,5 N and 2 N and particularly around 1,7 N.

Tables

TABLE 1

|  | Distal 1 | Distal 2 | Proximal |
| --- | --- | --- | --- |
| Material, Estane | ETE, X1014 | ETE, 60DT3 | 58212 |
| E-modulus (/MPa) | 1092 | 173 | 56 |
| Form | Circular | Circular | Circular |
| Outside diameter | 5.1 mm | 5.1 mm | 4.0 mm |
| Wall thickness | 0.35 mm | 0.35 mm | 0.67 mm |
| Rigidity in N (max force). | 27.6 (avg. of 3) | 14.4 (avg. of 3) | 1.4 (avg. of 7) |
| Method CP 3.2.6002 | (25.2-29.4) | (13.1-15.4) | (1.2-1.6) |
| Stiffness ASTM D747 | 994 Mpa | 186 Mpa |  |
| Hardness Shore D | 75 | 60 | 42 |

What is claimed is:

1. A catheter comprising:
a proximal section that is inserted into and telescopically movable relative to a distal section, a proximal end of the proximal section is rounded to remove sharp edges to adapt the rounded proximal end to be insertable into a urethra of a user and the distal section provides a discharge conduit for urine;
wherein the proximal section includes a rear portion, and an exterior surface of the rear portion diverges away from the proximal end to provide a diverging rear transition section that is wider than the proximal end of the proximal section;
wherein the distal section includes a front portion and an interior surface of the front portion converges to an opening formed in a front transition end, the opening is narrower than the diverging rear transition section of the proximal section.

2. The catheter of claim 1, wherein the proximal section includes a bump formed in a radial direction that is located between the diverging rear transition section and the proximal end, and the opening is narrower than the bump.

3. The catheter of claim 2, wherein the proximal section is inserted into the distal section in a collapsed configuration that locates the bump distal the opening, and the proximal section is movable to an expanded configuration that locates the bump proximal of the opening.

4. The catheter of claim 3, wherein the bump prevents the proximal section from moving from the expanded configuration to the collapsed configuration.

5. The catheter of claim 3, wherein the catheter is configured such that, when in the expanded configuration, a longitudinal force of 2 N or more applied to the proximal section toward the distal section deforms the proximal section to an unusable state.

6. The catheter of claim 3, wherein the bump provides a coupling in the expanded configuration that resists movement of the proximal section in a distal direction for longitudinal forces in a range from 5-10 N.

7. The catheter of claim 1, further comprising a hydrophilic coating.

8. A catheter comprising:

a proximal section that is inserted into a distal section to provide the catheter with a collapsed configuration, a proximal end of the proximal section is rounded and adapted for insertion into a urethra of a user and the distal section provides a discharge conduit for urine;

wherein the proximal section includes a rear portion, and an exterior surface of the rear portion diverges away from the proximal end to provide a diverging rear transition section that is wider than the proximal end of the proximal section;

wherein the distal section includes a front portion and an interior surface of the front portion converges to an opening formed in a front transition end, the opening is narrower than the diverging rear transition section of the proximal section;

wherein the proximal section includes an outward radial bump located between the diverging rear transition section and the proximal end, and the opening is narrower than the bump;

wherein the proximal section is movable from the collapsed configuration to an expanded configuration that locates the bump proximal of the opening, and the bump and the front transition end form a coupling that denies movement of the proximal section back to the collapsed configuration.

9. A catheter movable from a collapsed storage configuration to an expanded use configuration, the catheter extending axially in a longitudinal direction from a proximal end to an opposite distal end, the catheter comprising:

a proximal section insertable into a urinary channel, the proximal section extending axially between the proximal end and a distal transition end that is provided by a sleeve, and a distal section, a portion of which is insertable into the urinary channel, the distal section movable separately from the proximal section, the distal section extending axially between a second transition end and the distal end;

wherein the sleeve extends between the distal transition end to a head, with the distal transition end inserted inside the distal section of the catheter and the head inserted inside the proximal section of the catheter;

wherein the proximal section includes an outward radial bump located between the proximal end and the distal transition end of the sleeve.

10. The catheter of claim 9, wherein the sleeve has a shaft extending between the distal transition end and the head, and the head is an enlarged head having an outer diameter that is larger than an outer diameter of the shaft.

11. The catheter of claim 10, wherein the enlarged head of the sleeve contacts an inside surface of the proximal section of the catheter to support and define the outward radial bump of the proximal section.

* * * * *